United States Patent [19]

Stillman

[11] Patent Number: 4,551,332

[45] Date of Patent: * Nov. 5, 1985

[54] VITAMIN E COMPOSITIONS AND METHODS

[76] Inventor: Theodore Stillman, P.O. Box 63, Hardy, Ark. 72542

[*] Notice: The portion of the term of this patent subsequent to Oct. 18, 2000 has been disclaimed.

[21] Appl. No.: 542,645

[22] Filed: Oct. 17, 1983

Related U.S. Application Data

[63] Continuation-in-part of Ser. No. 290,157, Aug. 5, 1981, Pat. No. 4,410,517, which is a continuation of Ser. No. 151,627, May 20, 1980, abandoned.

[51] Int. Cl.$^4$ ................... A61K 35/78; A61K 31/355; A61K 47/00
[52] U.S. Cl. ................................. 424/195.1; 514/458; 514/784
[58] Field of Search ......................... 424/195, 284, 365

[56] References Cited

U.S. PATENT DOCUMENTS

| | | | |
|---|---|---|---|
| 2,582,395 | 1/1952 | Rigby | 424/284 |
| 2,628,930 | 2/1953 | Zentner | 424/284 |
| 3,244,595 | 4/1966 | Freigh | 424/237 |
| 4,410,517 | 10/1983 | Stillman | 424/195 |

FOREIGN PATENT DOCUMENTS 629433  11/1961  Canada ................................ 424/284

OTHER PUBLICATIONS

Handbook of Nonprescription Drugs, 6th ed., 1979, pp. 342, 408–410, 427, 429 and 463.

*Primary Examiner*—Albert T. Meyers
*Assistant Examiner*—John W. Rollins
*Attorney, Agent, or Firm*—Milton M. Field

[57] ABSTRACT

A dermatological coating material is prepared by combining a glyceryl stearate (glyceryl monostearate or glyceryl distearate) with a vitamin E component (α-tocopherol acetate, α-tocopherol and/or mixed tocopherols) to form a molten solution with the aid of heat, which solution, when cooled, forms a frozen solid or semi-solid solution at room temperature. The vitamin E component is hardened by this method. For some applications, the frozen solution is mixed or kneaded to eliminate or reduce crystal formation. In some embodiments, Jojoba oil is added as a third ingredient.

Utility as cosmetic bases, Vaseline substitutes, protective coatings, bandages, dermatological putties, carriers for germicidal or therapeutic agents, hair groomers, lubricants, such as sexual lubricants, stick cosmetics, such as lipsticks, and lip glosses is shown.

When α-tocopherol acetate is added to such solutions formed with α-tocopherol or mixed tocopherols, the unpleasant odors associated therewith are suppressed.

42 Claims, No Drawings

VITAMIN E COMPOSITIONS AND METHODS

This application is a continuation-in-part of my prior application Ser. No. 290,157, filed Aug. 5, 1981, now U.S. Pat. No. 4,410,517, Oct. 18, 1983, which application, in turn, is a continuation of application Ser. No. 151,627, filed May 20, 1980, now abandoned.

BACKGROUND OF THE INVENTION

1. Field of the Invention

This invention relates to frozen solutions of a glyceryl stearate with vitamin E ($\alpha$-tocopherol, $\alpha$-tocopherol acetate and/or mixed tocopherols) and, in some cases, Jojoba oil and the use of such solutions as cosmetic bases, protective skin coatings, substitutes for "Vaseline", dermatological putties, lubricants such as sexual lubricants, hair groomers, stick cosmetics and as carriers for therapeutic agents.

2. Brief Description of the Prior Art

There has been considerable interest in vitamin E and its supposed beneficial or therapeutic properties in skin preparations. This has resulted in the introduction of a number of products which use pure vitamin E as a dermatological coating. However, pure vitamin E has undesirable properties, such as its oiliness, when applied to the skin and the unpleasant odor of some forms of vitamin E.

While the applicant has no opinion as to special beneficial or therapeutic characteristics of vitamin E, it is nevertheless the case that there are many persons who are attracted to the use of vitamin E in skin preparations and this has led the applicant to investigate the problem of converting vitamin E to a form which is usable in skin and hair preparations.

Zentner U.S. Pat. No. 2,628,930 teaches the formation of aqueous emulsions of lipoid-soluble materials having vitamin E activity. $\alpha$-tocophol (a form of vitamin E) is warmed with glyceryl monostearate and other ingredients and converted to an emulsion while still in its molten state.

Brooks U.S. Pat. No. 3,253,992 is also primarily interested in preparing water emulsions and uses many compounds in his formulation in addition to vitamin E and glyceryl monostearate.

Rigby U.S. Pat. No. 2,582,395 discloses examples of ointments including small amounts (ten parts) of glyceryl monostearate and very small amounts (0.1 parts or less) of mixed natural tocopherols (vitamin E) in compositions containing peanut oil and/or lanolin primarily.

Hochberg U.S. Pat. No. 2,777,797 teaches the use of vitamin E or a mixture of natural tocopherols as part of an anti-oxidant in a composition for a dry carrier for fat-soluble vitamins.

Tingstad Canadian Pat. No. 629,433 uses glyceryl monostearate to prepare ointments with less than 1% of vitamin E and a predominance of other materials.

SUMMARY OF THE INVENTION

A dermatological coating material (a term used herein generically to describe a number of preparations applied to the skin or hair) is prepared by combining a glyceryl stearate with a vitamin E component (a term used herein generically to describe $\alpha$-tocopherol acetate, $\alpha$-tocopherol and mixed tocopherols) to form a solution with the aid of heat, which solution, when cooled, forms a frozen solid or semi-solid solution at room temperature. In this solution, the glyceryl stearate and the vitamin E are mutually soluable and do not separate on storage. The glyceryl stearate in one group of embodiments comprises glyceryl monostearate and in another group of embodiments comprises glyceryl distearate. For some applications, the frozen solution is mixed or kneaded to eliminate or reduce crystal formation. In some embodiments, Jojoba oil is added as a third ingredient; in these embodiments, the glyceryl stearate helps hold the Jojoba oil in solution.

Embodiments are described which are used as a cosmetic foundation or base, as a substitute for solid petrolatum, as a protective coating, as a bandage, as a dermatological putty, as a carrier for germicidal or therapeutic agents, as a hair groomer, as a lubricant, such as a sexual lubricant, as a stick cosmetic, such as a lipstick, and as a lip gloss.

The method according to the invention is a useful technique for hardening vitamin E.

The vitamin E component is usually in the form of $\alpha$-tocopherol acetate. $\alpha$-tocopherol or mixed tocopherols may be used, but because of their unpleasant odor cannot be used alone. It has been discovered, according to the present invention, that the use of $\alpha$-tocopherol acetate in combination with $\alpha$-tocopherol or mixed tocopherols result in the suppression of the unpleasant odor.

DETAILED DESCRIPTION

In the following detailed description, the following abbreviations are used: GMS for glyceryl monostearate; GDS for glyceryl distearate; ATA for $\alpha$-tocopherol acetate; AT for $\alpha$-tocopherol.

In general, the frozen solutions of the present invention will be manufactured by a method including the steps of:

(1) Putting all the ingredients into the same container and heating, preferably with steam, until the GMS melts and then mixing until a completely homogeneous solution is attained.

(2) When one considers the fragility of the vitamin E, it is advisable to bubble nitrogen or some other inert gas through the molten solutions or above the surface of all liquid vitamin E containing compositions. This is important for large batches and especially for compositions that contain the natural forms of vitamin E.

(3) The solution is permitted to cool to room temperature to form a frozen solution.

(4) In some cases it is necessary to mix a solution after it freezes to remove crystals. When this is called for, ordinary mixing will not suffice; such mixing requires pressure on the crystals. The only way to supply such pressure is to put the solution through a ball mill. The solution will be in a pipe with the solution having enough pressure on it to push a slightly fluid and still slightly warm partly frozen solution through a ball mill at just the right time after the homogeneous solution is formed. The right time is just after the molten solution freezes enough to form crystals but just before the molten solution becomes too frozen to be pumped through a pipe. This cooling requires some type of a cooling tower to remove the heat from piped solutions that come from a tank under pressure. Thus, large scale production that requires mixing after the molten solutions freeze are not simple to handle and mixing after a solution freezes is to be avoided if possible. It is, therefore, much simpler to pour the still molten homogeneous solution directly into their final containers and let them freeze in their final containers. There is a simple solution for the crystals that form in solutions that have Jojoba oil: aging, or aging with a slightly elevated temperature, approximately 95° F. Such aging could take as little as a few days. In this time, the crystals will disappear themselves.

Most of the compositions described herein are two separate entities:

(1) The crystalized product that results from freezing a molten solution. Solutions that are made from vitamin E do not show visible crystals, however, crystalization plays a role in pure vitamin E compositions. The entire solution is one crystal. Mixing vitamin E compositions in a ball mill will change the physical qualities of vitamin E solutions, because it removes the crystal formation and produces an amorphous frozen solution.

(2) The amorphous product of mixing is the second product that can result from most solutions that are described herein.

(3) A third product can result from the amorphous product of mixing, because aging the amorphous product of mixing will become partly recrystalized on aging. Thus, mixing (in a ball mill) and aging are important parts of the manufacturing procedures, particularly in the manufacture of lipsticks.

It should be pointed out that there are other ways to achieve the same results. For example, the GMS could be melted in a separate container and subsequently combined with the other ingredients with the aid of sufficient heat to keep the GMS molten until a homogeneous solution is obtained.

The preparation of a substitute for Vaseline from vitamin E and GMS or from GMS, ATA and Jojoba oil was a primary goal of parent application Ser. No. 290,157. The following describes the factors that have to be considered in preparing a substitute for Vaseline from vitamin E and GMS or GMS, vitamin E and Jojoba oil.

Jojoba oil is often a useful addition to GMS and ATA, because GMS and vitamin E solutions are highly tacky and Jojoba oil counteracts the tack. This raises the question as to what concentration of Jojoba oil is necessary and as to what criteria need be considered in making this determination.

Vaseline is fairly hard and viscous. Thus, warm, butter soft compositions that spread like a thin oil are not substitutes for Vaseline. Many of the Jojoba containing compositions are warm, butter soft. Vaseline is also translucent. If one adds too much GMS, the resulting composition is opaque. In addition, too much Jojoba oil will make the resulting solution opaque.

In view of the fact that the viscosity increases as the GMS concentration goes up, there is a conflict between the need to have translucent compositions and the need to have high viscosity. In solutions that have Jojoba oil, the situation is made more complex by the fact that Jojoba oil decreases viscosity. Thus, the need to reduce tack by adding Jojoba oil adds to the problems involved with the task of designing a substitute for Vaseline from GMS, vitamin E and Jojoba oil.

Another major consideration is the fact that pure GMS and ATA solutions are much more viscous or much harder than equivalent GMS, ATA and Jojoba oil solutions. Thus, increasing the concentration of vitamin E and decreasing the concentration or Jojoba oil will increase the viscosity or hardness of GMS, ATA and Jojoba oil compositions. However, increasing the concentration of vitamin E also increases tack. This is important, because the above substitute for Vaseline is to be used as a dermatological coating; and most people find tacky dermatological coatings obnoxious. This is complicated by the fact that the solutions that have high vitamin E and low Jojoba oil concentrations are most like Vaseline.

The following provides data that makes it possible to decide which formulations are most like Vaseline and which formulations resolve the above conflicts.

Pure GMS and vitamin E solutions have the advantage of being completely homogeneous. More important than this is the fact that GMS and vitamin E solutions are very stable. This means they do not separate into their components. This is not entirely true of solutions that contain Jojoba oil because solutions that contain 15% or less GMS tend to separate oil (see Table 1); whereas solutions that contain more than 20% GMS are resistant to bleeding Jojoba oil. However, solutions that contain only GMS and vitamin E never bleed oil and are always homogeneous and always crystal free. Thus, there are two big advantages to pure GMS and vitamin E compositions that contain no Jojoba oil: (1) pure GMS and vitamin E compositions are always homogeneous, whereas solutions that contain Jojoba oil may have to be mixed after the homogeneous matter solution freezes; and (2) pure GMS and vitamin E solutions (see Table 3) never bleed oils and never show separation of the ingredients from which the composition was made. Thus, GMS and vitamin E solutions are very stable. GMS and vitamin E solutions are also very viscous. This high viscosity approximates and/or exceeds the viscosity of Vaseline. For this reason, GMS and vitamin E solutions are excellent vehicles for suspending pigments, medications or perfumes, and can be used as foundations for cosmetics, because they can function as carriers for pigments and the like. The pigments do not settle out of solution. The same can be said for GMS, Jojoba oil and ATA solutions. All of the above is made possible because GMS is soluable with vitamin E and Jojoba oil in all proportions. The higher the concentration of vitamin E the less the likelihood that there will be separation of the Jojoba oil. Very high concentrations of vitamin E (above 60%) are least likely to show oil separation on long term storage when the GMS is below 20%. Such solutions are most likely to have viscosities that are high enough to resemble Vaseline and most likely to have the translucent quality that resembles Vaseline.

Thus, solutions that have no Jojoba oil and very low concentrations of GMS (below 15%) are most like Vaseline except for one quality: such solutions are very tacky. However, it is possible to imagine circumstances where the tackiness would be an advantage in that the skin would be protected longer and more efficiently by a tacky coating. Thus, there are two types of substitutes for Vaseline:

(1) a sexual lubricant (ATA, GMS and Jojoba oil).
(2) a protective skin coating (ATA and GMS).

As a matter of fact, one can change vitamin E from a liquid to a semisolid or a solid that is suitable for a stick cosmetic by simply increasing the concentration of the GMS that is dissolved in the vitamin E. One can also change vitamin E and Jojoba solutions from a liquid to a solid or semisolid by merely dissolving appropriate concentrations of GMS into the ATA and Jojoba oil solutions. Such transformations are possible, because GMS is soluable in all proportions in the above solutions. The fact that GMS is soluable in vitamin E in all proportions and will stay dissolved without separating when the solution cools is surprising for the following reasons: (1) Glycerin has three free hydroxide groups and glycerin is insoluable in vitamin E; (2) GMS has two free hydroxide groups and is thus very similar to glycerin, yet GMS is soluable in vitamin E; (3) vitamin E is soluable in glyceryl tristearate (fat), but glyceryl tristearate has no free hydroxide groups.

Since vitamin E is insoluable in pure glycerin, because glycerin has three free hydroxide groups, it would be expected that vitamin E would not be soluable in GMS, a compound that has two free hydroxide groups. However, it has been found according to the present invention that GMS is soluable in vitamin E. It has been proven that GMS is more than dissolvable in all proportions in the above solutions. GMS will stay in solution in all proportions when GMS is dissolved in pure vitamin E. The liquids will stay in most of the solutions that contain GMS, Jojoba oil and vitamin E. The ability of vitamin E and Jojoba oil to stay in solution is proven by the data in the following tables. There are, of course other surprises in this data.

In the following tables (and elsewhere in this specification) these abbreviations are used: GMS is glyceryl monostearate pure; ATA is alpha tocopherol acetate; JO is Jojoba oil; GR is grams in 100 grams of formulation; FP is freezing point in degrees Fahrenheit. The headings GMS, JO and ATA of vertical columns list the quantities in parts by weight of each ingredient. The columns headed A-J signify the following:

Column A lists a tack factor.
Column B lists a hardness factor when the solution is mixed in a ball mill.
Column C lists a hardness factor when the solution is unmixed.
Column D lists a reflectance factor when the solution is mixed in a ball mill.
Col. E lists a reflectance factor when the solution is unmixed.
Column F lists a transparency factor when the solution is mixed in a ball mill.
Column G lists a transparency factor when the solution is unmixed.
Column H lists a lubrication factor
Column I lists a reflectance factor when applied to the skin.
Column J lists a protectiveness factor.

The column headed "formulation" lists the formulation number. Where formulation numbers are omitted, the formulation was not relevant to the present disclosure.

TABLE 1

| FORMULATION | GMS | JO | ATA | FP | A | B | C | D | E | F | G | H | I | J |
|---|---|---|---|---|---|---|---|---|---|---|---|---|---|---|
| 2 | 10 | 80 | 10 | 98 | 1 | | | | | | | | | |
| 3 | 10 | 70 | 20 | 107 | 1 | | | | | | | | | |
| 4 | 10 | 60 | 30 | 112 | 1 | | | | | | | | | |
| 5 | 10 | 50 | 40 | 105 | 1 | | | | | | | | | |
| 6 | 10 | 40 | 50 | | 1 | | | | | | | | | |
| 7 | 10 | 30 | 60 | 102 | 1 | 0.5 | 0.9 | 0.9 | 0.9 | 0.8 | 0.9 | 0.8 | 0.9 | 0.8 |
| 8 | 10 | 20 | 70 | 100 | 1.2 | 0.6 | 0.8 | 0.9 | 0.9 | 0.8 | 0.8 | 0.9 | 0.9 | 1.2 |
| 9 | 10 | 10 | 80 | 98 | 1.8 | 0.9 | 0.9 | 0.9 | 0.9 | 0.9 | 0.9 | 0.9 | 0.9 | 1.2 |
| 10 | 15 | 15 | 70 | | 1.6 | 0.7 | 0.9 | 0.8 | 0.8 | 0.8 | 1.0 | 0.7 | 0.8 | 1.5 |
| 11 | 15 | 20 | 65 | | 1.2 | 0.8 | 1.1 | 0.8 | 1.1 | 0.8 | 0.7 | 0.9 | 0.9 | 1.2 |
| 12 | 17.5 | 11.5 | 71 | | 1.3 | 0.8 | 1.1 | 0.7 | 1.0 | 0.9 | 0.7 | 0.9 | 0.7 | 1.3 |
| 13 | 20 | 60 | 20 | 121 | 1.0 | 0.6 | 0.9 | 0.8 | 0.6 | 0.2 | 0.1 | 1.0 | 0.6 | 1.1 |
| 14 | 20 | 50 | 30 | 120 | 1.0 | 0.9 | 1.0 | 1.0 | 0.8 | 0.2 | 0.1 | 0.8 | 0.5 | 1.1 |
| 15 | 20 | 30 | 50 | 118 | 1.2 | 1.0 | 1.4 | 0.6 | 0.4 | 0.7 | 0.3 | 0.6 | 0.6 | 1.2 |
| 16 | 20 | 10 | 70 | | 1.6 | 1.3 | 1.4 | 0.7 | 0.5 | 0.8 | 0.7 | 0.7 | 0.6 | 1.3 |
| 17 | 20 | 20 | 60 | | 1.6 | 0.4 | 1.3 | 0.9 | 0.6 | 0.7 | 0.7 | 0.8 | 0.6 | 1.4 |
| 18 | 20 | 25 | 55 | | 1.5 | 0.8 | 1.3 | 0.7 | 0.5 | 0.8 | 0.8 | 0.8 | 0.6 | 1.4 |
| 21 | 25 | 55 | 20 | | 0.9 | 1.2 | 1.4 | 0.4 | 0.4 | 0.2 | 0.1 | 1.2 | 0.6 | 1.4 |
| 22 | 25 | 45 | 30 | | 1.1 | 1.2 | 1.4 | 0.5 | 0.3 | 0.2 | 0.1 | 1.3 | 0.6 | 1.4 |
| 23 | 25 | 35 | 40 | | 1.3 | 1.4 | 1.5 | 0.3 | 0.3 | 0.4 | 0.4 | 1.5 | 0.4 | 1.6 |
| 24 | 25 | 25 | 50 | | 1.6 | 1.3 | 1.6 | 0.7 | 0.6 | 0.6 | 0.5 | 0.7 | 0.4 | 1.6 |
| 25 | 25 | 65 | 10 | | 1.0 | 1.3 | 1.3 | 0.5 | 0.4 | 0.2 | 0.1 | 1.4 | 0.4 | 1.4 |
| 26 | 25 | 15 | 60 | | 1.5 | 1.5 | 1.6 | 0.4 | 0.3 | 0.6 | 0.4 | 0.6 | 0.7 | 1.8 |
| 27 | 30 | 25 | 45 | | 1.8 | 1.9 | 2.2 | 0.4 | 0.3 | 0.5 | 0.4 | 0.5 | 0.4 | 2.0 |

The numbers listed under vertical columns A–J are ratios between the characteristics of a sample and the characteristics of Vaseline. Considering the tack of a sample, for example, assume that Vaseline has a tack of 1.0 and the sample has a tack of 1.4, the resulting tack factor would be 1.4 divided by 1. A factor of 1.0 means that the sample and Vaseline have the same properties.

There was separation of the Jojoba oil in formulations 2 through 6 on storage (the Jojoba oil did not stay in solution). Beginning with formulation 7, no oil separation was observed. Formulations 13 and 14 were yellowish and opaque. Formulations 21 was smooth and homogeneous. Formulation 22 was homogeneous. Formulation 23 provided a heavy coating and crumbled slightly. Formulation 24 was slightly transparent. Formulation 25 was opaque. Formulation 26 was translucent.

These conclusions can be drawn:
1. Vitamin E will help hold the Jojoba oil in solution provided that there is enough vitamin E in the solution. Around 60% or more of the solution must be vitamine E (ATA), if the GMS is 10%.
2. The vitamin E may be facilitating the solution of Jojoba oil. However, it would seem that the concentration of GMS plays an important role in the process that keeps the Jojoba oil from separating from solution. This is supported by the fact that a small increase in the concentration of GMS had a profound effect on the ability of Jojoba oil to stay in solution. Thus, if one wanted to avoid separation of oil, one would increase the concentration of GMS. However, there is a factor that limits the concentration of GMS. This factor is transparency. An examination of Table 1 shows that the transparency of the solutions drop above a concentration of 20% for GMS. Thus, if one wishes to duplicate Vaseline, one is limited to solutions that have GMS concentrations that do not exceed approximately 25 grams in every hundred grams of composition. Even at that concentration the transparency of the resulting solution will be approximately one-half as transparent as Vaseline. See formulation 24. Formulations that have high Jojoba oil concentrations also have low transparencies. Another way to put it is, formulations that have high ATA concentrations tend to have high transparencies. The most outstanding formulation is not in Table 1. This formulation is as follows:

TABLE 2

| FORMULATION | GMS | JO | ATA | A | B | C | D | E | F | G | H | I | J |
|---|---|---|---|---|---|---|---|---|---|---|---|---|---|
| 34 | 20 | 40 | 40 | 1.2 | 1.0 | 1.0 | 0.8 | 0.7 | 0.4 | 0.3 | 1.0 | 0.7 | 1.4 |

The only disadvantage to formula 34 is the fact that it is about half as transparent as Vaseline and that it is only slightly more tacky than Vaseline. Otherwise, it has the same or better ability to lubricate and it offers much more protection than Vaseline. In addition, it is just about as hard as Vaseline and it does not make the skin reflect light as if it is covered with an oil or Vaseline, because the skin reflection is less than that of Vaseline.

Perhaps the most important consideration is tack. The solutions that have the highest tack are the solutions that do not have any Jojoba oil. The following table (Table 3) describes the GMS and ATA solutions in greater detail because pure GMS and ATA solutions contain the highest possible concentration of ATA, and because it is a goal to prepare a substitute for Vaseline that contains the highest possible concentrations of ATA. The following reasoning led to this search.

Pure vitamin E is being used extensively as a dematological coating. For reasons that are not yet apparent a significant percentage of the people are convinced that pure vitamin E is more effective than diluted vitamin E solutions. Unfortunately, pure vitamin E is a poor cosmetic, because pure vitamin E is a liquid and most women don't appreciate a well-oiled look. Thus, the problem is to transform ATA directly into a solid or semisolid that will be just as effective as pure vitamin E.

GMS and ATA are a possible solution to the above problem, because GMS is soluable in all proportions in ATA. This fact makes it possible to convert vitamin E directly into a foundation for solid or liquid or semisolid cosmetics. The most unexpected quality of ATA and GMS solutions is the fact that GMS and ATA remain dissolved in each other and do not separate into separate components. It is this remarkable stability of the resulting solution that was most unpredictable. This stability is remarkable because glycerol is completely incompatible with ATA; vitamin E does not dissolve in glycerol. It is the stability of GMS and ATA solutions that makes all its solutions useful. Without this stability the resulting solutions would be useless.

Other unexpected qualities of ATA and GMS solutions are proven by the facts revealed in the following table in which the column MPM lists the melting points in degrees Fahrenheit of mixed (in a ball mill) solutions and the column MPU lists the melting points of unmixed solutions.

TABLE 3

| FORMU-LATION | GMS | ATA | MPM | MPU | A | B | C | D | E | F | G | H | I | J |
|---|---|---|---|---|---|---|---|---|---|---|---|---|---|---|
| 44 | 5 | 95 | 83 | | 1.2 | 0.4 | 0.5 | 1.2 | | | 0.9 | 0.7 | 1.0 | 1.1 |
| 45 | 8 | 92 | 70 | | 1.2 | 0.6 | 0.7 | 1.1 | | | 1.0 | 0.6 | 1.0 | 1.2 |
| 46 | 10 | 90 | 94 | 106 | 1.3 | 0.8 | 0.8 | 1.0 | 0.8 | | 1.0 | 0.6 | 0.9 | 1.5 |
| 47 | 12 | 88 | | | 1.4 | 0.9 | 0.9 | 1.0 | 0.7 | | 1.0 | 0.6 | 0.9 | 1.5 |
| 48 | 15 | 85 | 100 | 108 | 1.7 | 1.0 | 1.0 | 1.0 | 0.8 | | 1.0 | 0.5 | 0.5 | 1.7 |
| 48A | 20 | 80 | | | 1.8 | 1.1 | 1.5 | 0.9 | 0.6 | | 0.7 | 0.4 | 0.4 | 1.7 |
| 49 | 25 | 75 | 112 | 112 | 1.9 | 1.2 | 2.0 | 0.8 | 0.5 | | 0.5 | 0.3 | 0.3 | 1.8 |
| 50 | 30 | 70 | 114 | 114 | 2.0 | 1.2 | 2.0 | 0.7 | 0.5 | | 0.5 | 0.3 | 0.2 | 2.5 |
| 51 | 40 | 60 | 115 | 115 | 3.0 | 1.8 | 2.5 | 0.4 | 0.3 | | 0.3 | 0.1 | 0.1 | 3.5 |
| 52 | 50 | 50 | 117 | 117 | 3.0 | 3.0 | 3.0 | 0.1 | 0.1 | | 0.1 | 0.1 | 0.1 | 4.0 |
| 53 | 60 | 40 | 118 | 118 | 2.5 | 1.6 | 4.0 | 0.0 | 0.0 | | 0.0 | 0.0 | 0.0 | 4.0 |
| 54 | 90 | 10 | | 124 | Hard and unmalleable homogeneous |
| 55 | 99 | 1 | | 129 | Hard and unmalleable homogeneous |
| 56 | 70 | 30 | | 120 | Hard slightly tacky malleable |
| 57 | 80 | 20 | | 122 | Hard even less tacky and less malleable |
| 58 | 4 | 96 | | 50 | Viscous liquid at room temperature |

These conclusions may be drawn from Table 3:
1. The lower the concentration of GMS the more like Vaseline the GMS and ATA solutions will be.
2. Note that solutions with 5, 8, 10, 12, 15 and 20% GMS have tacks that are only slightly higher than that of Vaseline. Also note that these same samples are as transparent as Vaseline and are as reflective and hard as Vaseline. Thus, outwardly these samples look like Vaseline. However, these same samples, with 5 to 30% GMS concentration have less ability to lubricate than Vaseline. However, the ability to lubricate is enhanced by body fluids. In fact, all GMS and ATA solutions that are malleable can be spread upon the skin. If they can be spread upon the skin, they will provide some lubrication because the tack is completely eliminated by water on the surface of the coating.

This raises a new concept. GMS and ATA solutions are actually two separate solutions. One solution is the unmixed solution and the other solution is the mixed solution. There is apparently some type of crystal structure in the unmixed solutions. This crystal structure raises melting points and reduces tack and makes the solutions harder. The most pertinent difference stems from the fact that mixing or kneading the solutions changes the solid GMS and ATA solutions. The primary effect of kneading or mixing GMS and ATA solutions is: (1) an increase in tack; and (2) a decrease in hardness.

This change is particularly important for the solutions that have GMS concentrations above 40%. Such solutions are solids and, at first glance, they appear to be unspreadable upon the skin. However, these solutions are malleable. They can be kneaded until all the crystal structure within them is eliminated. The resulting solutions are soft enough to spread upon the skin, and they look like putty and spread like putty. The most dramatic thing about this putty is in its enormous increase in tack as compared with the crystalized or unmixed solutions. Thus, the effect of mixing solid, above 40% GMS containing GMS and ATA solutions is to transform a hard non-spreadable non-tacky substance into a soft, spreadable, and very tacky putty. The resulting putty can be rolled into balls or spread upon the skin where it sticks very tenaciously. The resulting coating is very lasting and can be applied in any thickness. The result is a skin putty that is extremely malleable to any thickness and which provides a highly lasting protective coating for the skin. Such solutions are opaque and white. Thus, they could be used to camouflage skin abnormalities. The surface of these coatings are tacky enough to be coated with a face power. In addition, the resulting coating is flexible and it can be applied in very thick coatings. Thus, the result is a skin putty that can be used to camouflage or protect skin abnormalities.

Thus, solutions of ATA and GMS are usable as a substitute for Vaseline in the following concentration ranges: GMS 5% to 30%; ATA 95% to 70%. GMS and ATA solutions are also useful as a dermatological putty. Table 3 indicates that solutions that have approximately 90% GMS and 10% ATA are not malleable. Thus, all solutions that contain 30% GMS to 80% GMS and 70% to 20% ATA are suitable for use as a dermatological putty.

The primary advantage of dermatological putty is its tenacious ability to adhere to the skin. This is probably due to the fact that Table 3 shows that the tack increases as the concentration of GMS increases. Thus, increased tack means that the coating will have increased ability to adhere to the skin. Since increased ability to adhere to the skin means increased ability to protect the skin, GMS and ATA solutions are dermatological coatings that offers superior ability to protect the skin. This fact is substantiated by the fact that it is very difficult to remove the dermatological putty from the skin. Even soap and water is resisted to some degree. It has been found that dermatological putty may be used as a substitute for Bandaids. This will be true during the initial phases following an injury. However, the final healing phases require exposure to the air.

As a matter of fact, all of the possible solutions of GMS and ATA have been tried as protective coatings for a large variety of wounds. All of these solutions have been found effective as substitutes for Bandaids during the initial phases following the injury. The most effective solution was dermatological putty because it was not as easily removed from the wound.

The addition of germicidal agents facilitates the wound protective qualities of GMS and ATA solutions. Clove oil can be added to GMS and ATA solutions, and it seems to be soluable in GMS, ATA and Jojoba oil solutions in all proportions. In addition, clove oil also seems to be resistant to oxidation. In view of the fact that clove oil has a high phenol coefficient, only a small percent of the GMS and ATA solutions need be clove oil. The following table describes the effect of clove oil.

TABLE 4

| FORMU-LATION | INGREDIENT CONCENTRATIONS IN GRAMS | | | PERCENT CLOVE OIL | MELTING POINTS |
|---|---|---|---|---|---|
| | GMS | ATA | CLOVE OIL | | |
| 59 | 10 | 90 | 0 | 0 | 102 |
| 60 | 10 | 90 | 4.0 | 3.85 | 96 |
| 61 | 30 | 70 | 1.5 | 1.48 | 110 |
| 62 | 30 | 70 | 0 | 0 | 112 |
| 63 | 50 | 50 | 1.5 | 1.48 | 116 |
| 64 | 50 | 50 | 0 | 0 | 118 |
| 64A | 40 | 60 | 9.09 | 106 | |
| 64B | 33 | 67 | 0.3 | .299 | 115 |

All the other physical qualities for the solutions described in Table 4 are the same. All solutions are homogeneous and show no oil separations.

From this it is concluded that the addition of one or two percent clove oil is well tolerated in the formulations described in Table 3, and such an addition will only cause a slight lowering of the freezing point of such solutions. The higher the concentration of clove oil, the greater is the effect on freezing point. Formulation 63 is probably the optimum formulation for dermatological putty. It is medicated with clove oil. Thus it is suitable for medicating minor skin abraisons and protecting them from the environment during the initial phases of the healing process, and it is the initial phase of the healing process that the wound is most liable to infection.

Formulations 60 and 61 are salve-like ointments that can also provide temporary protection for minor abrasions or burns. However, these formulations do not adhere to the skin as well as formulation 63.

All of the GMS and ATA or GMS, ATA and Jojoba oil solutions are high viscosity solutions. Thus, these solutions are ideal for suspending solids especially if they are finely gound or −200 mesh material. Such suspended solids are highly resistant to settlement.

There is a reason for prefering ATA over AT or the mixed tocopherols. Both AT and the mixed tocopherols stink; their odors are truly obnoxious. In addition, ATA is much more stable. Thus, ATA is the best form of vitamin E to use in formulations that are to be used as substitutes for Vaseline simply because ATA does not stink.

However, there are good reasons for incorporating some AT or mixed tocopherols. AT and the mixed tocopherols are anti-oxidants simply because they are easily oxidized. ATA is resistant to oxidation and does not function as an antioxidant. Thus, it might be advantageous to incorporate a small amount of AT or mixed tocopherols into formulations that are made from ATA or ATA and Jojoba oil in order to supply a readily oxidizable vitamin E to function as an anti-oxidant.

The following formulations show the effects of adding AT or the mixed tocopherols to some of the above formulations in concentrations of approximately 2%.

TABLE 5

| FORMULA | GMS | ATA | JO | AT | MIXED TOCOPHEROLS | MPU |
|---|---|---|---|---|---|---|
| 65 | 10 | 88 | 0 | 2 | | 106 |
| 66 | 10 | 88 | 0 | | 2 | 106 |
| 67 | 25 | 73 | 0 | 2 | | 112 |
| 68 | 25 | 73 | 0 | | 2 | 112 |
| 69 | 40 | 58 | 0 | 2 | | 115 |

TABLE 5-continued

| FORM-ULA | GMS | ATA | JO | AT | MIXED TOCOPHEROLS | MPU |
|---|---|---|---|---|---|---|
| 70 | 40 | 58 | 0 | | 2 | 115 |

O is hardness for mixed solutions.
P is transparency for unmixed solutions.
Q is transparency for mixed solutions.
R is lubrication.
MPF is melting point in degrees Fabrenheit.
MT is mixed tocopherols.

TABLE 6

| FORMULA | MPF | *GMS | *MT | *ATA | *AT | K | L | M | N | O | P | Q | R |
|---|---|---|---|---|---|---|---|---|---|---|---|---|---|
| 71 | 110 | 50 | 50 | | | 0.0 | 0.0 | 3.0 | 4.0 | 1.0 | 0.0 | 0.0 | 0.1 |
| 72 | 117 | 50 | | 50 | | 0.3 | 0.0 | 3.0 | 4.0 | 1.0 | 0.3 | 0.4 | 0.5 |
| 73 | 111 | 50 | | | 50 | 0.1 | 0.1 | 3.0 | 3.8 | 1.0 | 0.1 | 0.1 | 0.1 |
| 74 | 92 | 25 | 75 | | | 0.4 | 1.3 | 1.7 | 2.0 | 1.3 | 0.7 | 0.6 | 0.7 |
| 75 | 113 | 25 | | 75 | | 0.4 | 1.3 | 1.7 | 2.0 | 1.3 | 0.7 | 0.7 | 0.7 |
| 76 | 92 | 25 | | | 75 | 0.5 | 1.3 | 1.7 | 1.8 | 1.2 | 0.6 | 0.6 | 0.8 |
| 77 | 82 | 15 | 85 | | | 0.9 | 0.3 | 1.2 | 1.2 | 0.7 | 0.7 | 0.8 | 0.8 |
| 78 | 100 | 15 | | 85 | | 0.9 | 1.3 | 1.8 | 1.5 | 1.1 | 0.7 | 0.6 | 0.8 |
| 79 | 83 | 15 | | | 85 | 1.0 | 0.5 | 1.4 | 1.0 | 0.8 | 0.8 | 0.8 | |
| 80 | 122 | 67 | 33 | | | 0.1 | 0.8 | 1.1 | 2.5 | | 0.1 | 0.1 | 0.1 |
| 81 | 120 | 67 | | 33 | | 0.0 | 0.9 | 1.0 | 2.4 | 0.9 | 0.1 | 0.1 | 0.1 |
| 82 | 122 | 67 | | | 33 | 0.1 | 0.9 | 1.2 | 2.2 | 1.0 | 0.1 | 0.1 | 0.1 |
| 83 | 83 | 5 | | 95 | | 1.2 | 1.3 | | 0.5 | | 0.9 | | 0.7 |
| 84 | | 5 | | | 95 | **Liquid at 40° F. | | | | | | | |
| 85 | | 5 | 95 | | | **Liquid at 40° F. | | | | | | | |
| 86 | 66–82 | 8 | 92 | | | 0.9 | | 1.0 | 0.8 | | 1.0 | | 0.9 |
| 87 | 65–84 | 8 | | | 92 | 0.8 | | 1.0 | 0.8 | | 1.0 | | 0.8 |
| 88 | 62 | 3 | | 97 | | 1.0 | 1.3 | | 0.5 | | 1.0 | | 0.8 |
| 89 | | 2 | | 98 | | Still liquid at 38° F. | | | | | | | |

*In grams
**Sample will set up or solidify if allowed to stand at room temperature overnight.

Obviously, there are, at best, only slight effects on the melting point from adding AT or mixed tocopherols.

Most of this specification has dealt with solutions of GMS and ATA. This is true because ATA is the most stable form of vitamin E, because GMS pure is biodegradeable and because there are no other compounds associated with GMS pure. For example, acid stable GMS has polyethylene glycol monostearate associated with the GMS. Polyethylene glycol monostearate is not a normal part of the biochemical processes within living cells. Thus, there are no enzymes within the living cells to biodegrade polyethylene glycol monostearate. In view of the fact that one of the primary goals of this invention is to duplicate Vaseline's ability to function as a sexual lubricant without suffering from the primary disability of Vaseline (that Vaseline collects within a woman's female organ system, because Vaseline is not biodegradeable), polyethylene glycol monostearate may suffer from the same problem that confronts Vaseline in that it is also not biodegradeable and it also will collect within a woman.

Self-emulsifying GMS is associated with potassium stearate. Potassium stearate is a soap and soap is a potential source of irritation. Thus, on theoretical grounds alone there is only one usable GMS and that is GMS pure. This is true, because GMS pure is the only GMS that is innocuous.

The other forms of vitamin E are a different story, because pure AT and the mixed tocopherols are also capable of forming the above types of vitamin E and GMS solutions. Table 6 shows that GMS is soluable in all proportions in AT (pure) and the mixed tocopherols. This table also describes the range of possible solutions.

The following table compares GMS and vitamin E solutions that contain the following types of vitamin E: AT, ATA and the mixed tocopherols (MT). In this table, the column headings K–R represent these factors:
K is reflectance for mixed solutions.
L is tack for unmixed solutions
M is tack for mixed solutions.
N is hardness for unmixed solutions.

Table 6 shows that the samples that are mixed have a dramatic drop in hardness. The higher the concentration of the GMS, the more profound the drop in viscosity. This could only mean that the crystal structure formed when molten GMS and vitamin E are cooled is primarily due to a reaction between GMS and vitamin E. The higher the concentration of GMS, the more like GMS is the resulting GMS and vitamin E solution, provided the sample is not mixed.

Formulas 86 and 87 list two temperatures. The lower number is the freezing point; the higher number is the melting point. The freezing and melting points are different, because some sort of crystalization occurs after the sample's freezing point is reached. Thus, the freezing point is not the same as the melting point. The melting point is higher. Thus, formula 86 has a freezing point of 66 and a melting point of 82. The difference could only be due to the energy needed to break down the chemical bonds created during crystalization. These factors indicate that crystalization plays a major role in the characteristics of GMS and vitamin E solutions. It is believed that the GMS, Jojoba oil, and vitamin E solutions will form crystals initially. However, storage for approximately a day or more will cause the crystals to disappear *without mixing*. This is probably due to some new intermolecular bonding that occurs during storage. The formation of these new bonds apparently breaks down the crystals that form when molten GMS, Jojoba and vitamin E solutions freeze. Most chemists would not have noticed that the crystals break down in *storage*.

GMS and vitamin E solutions do not exhibit any crystals, and yet despite the lack of visible crystals there is a significant difference between the freezing point and melting point. There is apparently some sort of outwardly invisible chemical bonding formed between GMS and vitamin E. This bonding is apparently broken when the solutions are mixed. However, once the bonding is broken by mixing, there is a profound increase in tack for all the GMS and vitamin E solutions. This profound increase in tack is apparently limited to GMS and vitamin E solutions. These facts are particularly important to solutions that are used as dermatological putties.

Tack is also particularly important to hair grooming aids, because it takes a little tack to hold the hair in place. Since GMS and vitamin E solutions are tacky, GMS and vitamin E solutions are very useful as hair grooming aids. Hardness is also important to a hair groomer. An examination of Table 3 indicates that the hardness of GMS and ATA solutions increases as the concentration of the GMS increases. However, the tack also increases as the GMS concentrations increase. In addition, the hardness and tack is dependent on whether the solutions are mixed.

Without knowledge of the effects of mixing, one might assume that the solution that has 30 grams of GMS and 70 grams of ATA is useless for hair grooming because it is too hard and too lacking in tack. However, mixing this solution completely changes these characteristics. See formulation 50 in Table 3. This formula can be softened by kneading and then spread on the hair.

Another unusual characteristic of GMS and vitamin E solutions is that mixed solutions will harden on standing. Once they harden the tack is again reduced. This last point is important to hair grooming, because one needs the tack to groom the hair. However, once the hair is properly groomed too much tack makes the hair feel tacky. Fortunately, the mixed GMS and ATA solutions form a slightly harder and less viscous solidified solid as it ages. Thus, the hair becomes less tacky within a short time after the grooming aid is applied. Hence, GMS and vitamin E when mixed in appropriate concentrations is an effective hair grooming aid. The useful range of GMS and vitamin E solutions lies between solutions A and B: A includes three grams GMS and 97 grams vitamin E; B includes 35 grams GMS and 65 grams vitamin E. Solutions that are above 40 grams of GMS in 100 grams of solution are too hard to be used as hair groomers even after they are mixed.

Table 6 indicates that solutions with the mixed tocopherols and AT have approximately the same tack as solutions with ATA. Thus, all the different forms of vitamin E and all the possible mixtures of the different forms of vitamin E can produce GMS and vitamin E solutions that can be used as hair groomers or dermatological putties in the concentrations that lie between those of solutions A and B described above. The solid GMS and mixed tocopherols and the solid GMS and AT solutions can also be kneaded from a hard non-pliable, non-tacky substance to a soft pliable tacky substance that can be spread on the skin. Thus, all the different forms of natural vitamin E can be kneaded into a dermatological putty as defined herein.

An examination of Table 1 indicates that some of the solutions that have Jojoba oil, GMS, and vitamin E have adequate enough tack to be used as a hair groomer. The following pattern emerges. Formula 9 and 10 indicates that low concentrations of GMS will tolerate only 10 to 15 grams of Jojoba oil in 100 grams of formulation. At these levels, formulas 9 and 10 (Table 1) have a tack of 1.8 and 1.6. If the GMS concentration is increased to 20%, the Jojoba oil concentration can be increased to 25%. Thus, as has already been indicated, the higher the concentration of GMS, the higher the tack and the higher the concentration of Jojoba oil can be.

However, if we change the objectives and decide to prepare a lubricant, it is plain to see that formulas 13 and 14 will be preferred to 16 and 17. Formulas 13 and 14 have the same hardness as Vaseline, the same tack as Vaseline, and the same ability to lubricate as Vaseline. Also, it reflects light or is as shiny as Vaseline. However, it is certainly not as transparent as Vaseline. In fact, one could well consider the composition to be opaque.

A further examination of Table 1 will indicate that transparency is a function of the concentration of Jojoba oil. A solution with even 30% GMS will be half as transparent as Vaseline, if the concentration of Jojoba oil is no higher than 25 grams of Jojoba oil in each 100 grams of GMS, Jojoba oil and vitamin E composition. If the GMS, Jojoba oil and vitamin E compositions contain more than 25 grams of Jojoba oil in 100 grams of said composition, the composition will be too opaque to be a clear substitute for Vaseline. However, it can still function as an adequate sexual lubricant. For example, formulations 21 to 23 are at least equal to Vaseline in the ability to lubricate, are only slightly more tacky than Vaseline, and are very similar to Vaseline in such characteristics as hardness and reflectivity. Thus, formulations 21 to 23 can indeed function as substitutes for Vaseline, even if they are more opaque than Vaseline.

As to Table 3, an examination of the vertical columns indicates that the compositions with the lowest concentration of GMS have the highest ability to lubricate, the lowest tack, the highest transparency, and the highest reflectivity. In addition, most of the readings are close to or equal to 1. This means that the compositions that have the lowest concentration of GMS are also the compositions that are most like Vaseline. This is fortunate, because a primary objective of this invention is to prepare a composition that resembles Vaseline, and that has the highest possible concentration of vitamin E. In other words, the original quest began with the observation that many people prefer to put pure vitamin E o their skin. In view of the fact that pure vitamin E is a viscous oil that is a poor cosmetic, there is a need for a way to transpose pure vitamin E directly into a cosmetic.

Table 6 also provides an answer to the need for a way to transpose vitamin E directly into a cosmetic. Formula 88 shows that only three grams GMS dissolved into 97 grams of ATA will transform ATA into a semisolid that can function as a substitute for Vaseline. Thus, I have discovered a possible substitute for Vaseline that is as close as possible to pure vitamin E in that it has over 97 parts vitamin E in 100 parts of composition.

The mixed tocopherols and AT both require at least 5% GMS to harden the vitamin E. Thus, GMS and ATA are the best possible ingredients for preparing a solidified vitamin E that has the highest possible concentration of vitamin E.

Table 6 compares the three types of vitamin E: mixed tocopherols, AT, and ATA. This comparison indicates that these three types of vitamin E produce solutions with GMS that have similar physical characteristics or that are more or less similar in all the possible concentrations of GMS, except for GMS concentrations below 8%. For some strange reasons, the mixed tocopherols require more GMS to harden the below 8% GMS solutions. Compare formulations 83, 84 and 85.

Also note that formula 88 is solid and formula 89 is liquid. Thus, ATA is liquid at 2% GMS concentration, whereas the mixed tocopherols require several hours to harden when the concentration of the GMS is approximately 5%. Mixed tocopherols and AT both do not harden at 85% GMS concentrations. This is probably due to the fact that mixed tocopherols and ATs both have soya oil left in them. Probably one-third of their mass is soya oil. This is due to the fact that they are both produced by the distillation process. Actually, these samples will harden if allowed to set for approximately twenty-four hours. Thus, the 5% GMS solution is not liquid.

Table 3 shows that GMS is soluable in ATA in concentrations that range from 1 to 99 grams in 100 grams of the GMS ATA solution. Thus, GMS and ATA are soluable in all proportion in each other with the aid of heat. Table 6 shows that GMS is soluable in mixed tocopherols and AT in all proportions.

In Table 7, which follows, all ingredients are given in grams. The column heading MP stands for melting point in degrees Fahrenheit; MT is mixed tocopherols; S is the hardness factor for unmixed solutions; T is the transparency factor; U is the lubrication factor; and V is the tack for mixed solutions.

TABLE 7

| FORMULA | MP | GMS | MT | ATA | AT | S | T | U | V |
|---|---|---|---|---|---|---|---|---|---|
| 90 | 114 | 50 | 25 | 25 | | 4.0 | 0.0 | 0.1 | 3.0 |
| 91 | 114 | 50 | | 25 | 25 | 4.0 | 0.0 | 0.1 | 3.0 |
| 92 | 102 | 25 | 37 | 38 | | 2.0 | 0.7 | 0.7 | 1.3 |
| 93 | 91 | 15 | 42 | 43 | | 1.2 | 0.7 | 0.8 | 1.0 |
| 94 | 91 | 15 | | 43 | 42 | 1.2 | 0.7 | 0.8 | 1.0 |

All the formulations in Table 7 are miscible in one another. The resulting solutions will have properties that are approximately the average of solutions that are combined.

In Table 8, MT represents mixed tocopherols; FP is freezing point; and column headings W, S, Y, Z, and AA represent, respectively, tack, hardness, transparency, lubrication and reflectivity factors.

TABLE 8

| FORMULA | MT | ATA | AT | GMS | FP | W | X | Y | Z | AA |
|---|---|---|---|---|---|---|---|---|---|---|
| 103 | 92 | | | 8 | 62 | 1.0 | 0.8 | 1.0 | 0.8 | 0.8 |
| 104 | 85 | | | 15 | 83 | 1.2 m | 1.2 u | 0.7 u | 0.8 | 0.8 |
| 105 | 75 | | | 25 | 92 | 1.7 m | 2.0 | 0.7 | 0.7 | 0.4 |
| 106 | 60 | | | 40 | 104 | 1.0 | 0.1 | 0.3 | 0.6 | 0.0 |
| 107 | 33 | | | 67 | 122 | 1.2 | 3.5 | 0.1 | 0.1 | |
| 108 | 50 | | | 50 | 110 | 3. m | 3.0 | 0.0 | 0.1 | 0.0 |
| 109 | | 92 | | 8 | 90 | 1.2 | 0.7 u | 1.0 | 0.6 | |
| 110 | | 90 | | 10 | 94 | 1.3 | 0.8 m | 1.0 | 0.6 | 0.8 |
| 111 | | 85 | | 15 | 100 | 1.7 | 1.0 | 1.0 u | 0.5 | 0.8 u |
| 112 | | 75 | | 25 | 113 | 1.9 | 2.0 u | 0.5 u | 0.3 | 0.2 |
| 113 | | 50 | | 50 | 115 | 3.0 m | 3.0 | 0.1 u | 0.1 | 0.1 |
| 114 | | 40 | | 60 | 118 | 2.5 | 1.6 m | 0.0 | 0.0 | 0.0 |
| 115 | | 10 | | 90 | 124 | Unmalleable, unusable | | | | |
| 116 | | | 94 | 6 | 64 | 1.3 | 0.5 | 1.0 | 0.8 | 0.9 |
| 117 | | | 85 | 15 | 70 | 1.6 | 0.8 | 0.7 | | 0.9 |
| 118 | | | 75 | 25 | 92 | 1.8 m | 2.2 | 0.8 | 0.8 | 0.4 |
| 119 | | | 60 | 40 | 98 | 1.7 | 1.5 | 0.3 | 0.7 | 0.6 |
| 120 | | | 50 | 50 | 104 | 3.0 m | 3.0 | 0.0 | 0.1 | 0.0 |

In columns W, X, Y and AA the addition of "m" and "u" designate, respectively, that the sample in question was mixed or unmixed.

The melting point of formula 103 was 82° F.

A number of conclusions may be drawn from Table 8. The ATA solutions have freezing points that are higher than those of the mixed tocopherols and the AT solutions. Despite the differences in freezing points, all equivalent vitamin E and GMS solutions have fairly similar physical properties regardless of what type of vitamin E is used. However, there are other considerations. The ATA solutions are more resistant to oxidation, and the mixed tocopherols and AT solutions have an obnoxious odor. ATA and Jojoba oil have no odor. The higher the concentration of GMS, the harder the resulting solution. GMS is soluable in all proportions in all of the solutions. It would seem the Jojoba oil is kept from separating from the GMS, Jojoba oil and vitamin E solution by the GMS. This is strange, because GMS would normally be considered the solute and vitamin E and Jojoba oil, being liquids, would be considered the solvents. If vitamin E and Jojoba oil are solvents, adding more Jojoba oil and vitamin E would make the solute, GMS, more soluable. It would seen that GMS is not dissolved in the Jojoba oil and vitamin E. This is proven by formulations 2 to 6, because these formulations start out as solid solutions that will on storage separate, or bleed.

The most potent form of vitamin E is natural AT. Natural vitamin E is D alpha tocopherol concentrate. The word concentrate means it is distilled from natural oils. Unfortunately the distillation process does not permit the separation of absolutely pure vitamin E. One of the most concentrated natural D alpha tocopherol solutions on the market is Eastman E 5-67 manufactured by Eastman Co. The following table describes the range of useful solutions that can be prepared by dissolving GMS into Eastman E 5-67. This table is particularly important for those who wish to put a composition on their skin that has the highest possible potency of natural vitamin E contained within it. While it is not known why a significant number of people are putting pure vitamin E on their skins, such people will be attracted to the highly concentrated D alpha tocopherol solutions of the invention that are semisolids or solids. It is true that natural AT stinks. However, this odor can be masked with perfumes; or as will be demonstrated elsewhere in this disclosure, the incorporation of ATA with the AT will mask the unpleasant odor.

The term "natural" needs to be further defined. Artificially made AT includes two isomers, D and L. The L isomer is not used by the body. Only the D isomer is usable in living biochemical processes. Eastman E 5-67 is pure D isomer alpha tocopherol plus about 30% soya oil that cannot be removed by the distillation process. Thus, Eastman E 5-67 is the most concentrated source of D alpha tocopherol even though it has soya oil, because it is pure D isomer. ATA is an equal mixture of the D and the L isomers. Thus, ATA only contains 50 grams of the D isomer in 100 grams of ATA.

A comparison of the freeze points of ATA solutions on Table 3 with the freeze points of the AT solutions listed in Table 9 (below) indicates that the freezing point of GMS and AT is lower than that of GMS and ATA (when one compares solutions that have the same GMS concentrations). This probably indicates why the addition of AT seem to lower the freezing point of equivalent solutions. See the formulations of Table 10 below.

The most amazing thing about AT solutions is their ability to make ATA, Jojoba oil and GMS solutions more transparent. See the formulation of Table 10. Jojoba oil seems to make GMS and ATA solutions more opaque. However, Jojoba oil is needed to reduce tack. Now there seems to be one more additive that will reduce the tendency for Jojoba oil to make solutions opaque.

While it is true that AT and the mixed tocopherols have an obnoxious odor, it appears that GMS and ATA solutions seem to mask the odor of AT solutions. This is proven by the formulations of Table 10, which formulations have no odor.

It is to be noted that all malleable GMS solutions with ATA, AT or mixed tocopherols can be mixed into a soft putty and used as a dermatological putty. In other words, the solid unmixed GMS and vitamin E (ATA, AT or mixed tocopherols) solutions are not tacky; only mixing or kneading will make these solutions tacky. Thus, all the solid GMS and vitamin E solutions can be kneaded into soft tacky putty that can be put on the skin much like ordinary putty can be spread on the skin.

Oxidation of D alpha tocopherol is a big problem. Expensive packaging to keep oxygen out may be the only solution. This may put D alpha tocopherol at a price disadvantage, because D alpha tocopherol that is highly purified costs twice as much as ATA. If we add the price of expensive packaging to the price of D alpha tocopherol, the result could be a price that could not compete with a product made from ATA.

The second type of vitamin E needs to be considered: the mixed tocopherols. This vitamin E contains alpha, beta, and gamma isomers or vitamin E entirely in dextro rotary configuration, because it is also distilled from natural oils.

Of the three types of vitamin E, the ATA is the most stable and, in addition, has no odor and no color. The natural vitamin E's are yellow and have an unpleasant odor.

Stability and shelf life is of enormous importance to a commercially sold product and this may very well decide the issue as to which vitamin E preparation is to be used.

However, the natural vitamin E's are anti-oxidants. Thus, the natural vitamin E's may be used in the end in low concentrations (1 to 2%), just to protect ATA solutions simply because ATA solutions are so resistant to oxidation that they do not act as anti-oxidants.

On the other hand, further medical research may produce evidence to support the contention that the natural vitamin E's (dextro rotary) have a therapeutic benefit that will make the highly concentrated natural vitamin E's the preferred cosmetic base. In this case, my discovery that ATA masks the obnoxious odor of the natural vitamin E's, could be of great importance.

In Tables 9, 10 and 11 the headings BB, CC, DD, EE and FF, respectively, designate hardness factors for unmixed solutions, tack factors for unmixed solutions, lubrication factors, pressure responsive characteristics, and rub-off characteristics. The headings GG, HH, II and JJ indicate hardness, tack, transparency and reflectivity characteristics. FP designates freezing point in degrees Fahrenheit.

TABLE 9

| FORMULATIONS MADE FROM D ALPHA TOCOPHEROL | | | | | | | | |
|---|---|---|---|---|---|---|---|---|
| FORMULA | GMS | AT | FP | #BB | #CC | #DD | #EE | #FF |
| 121 | 80 | 20 | 110 | 4.0 | 0.7 | 0.1 | 4.0 | 0.0 |
| 122 | 70 | 30 | 108 | 3.0 | 0.8 | 0.1 | 3.0 | 0.1 |
| 123 | 60 | 40 | 106 | 2.0 | 1.2 | 0.2 | 2.0 | 0.2 |
| 124 | 50 | 50 | 104 | 1.8 | 1.3 | 0.5 | 1.5 | 0.5 |
| 125 | 40 | 60 | 98 | 1.2 | 1.4 | 0.6 | 1.4 | 0.7 |
| 126 | 33 | 67 | 96 | 1.0 | 1.5 | 0.7 | 1.3 | 0.8 |
| 127 | 25 | 75 | 92 | 0.8 | 1.6 | 0.9 | 1.1 | 0.9 |
|  |  |  |  | +GG | +HH | +II | +DD | +JJ |
| 128 | 20 | 80 | 86 | 1.5 | 2.0 | 0.3 | 0.5 | 0.5 |
| 129 | 15 | 85 | * | 1.0 | 1.6 | 0.7 | 0.7 | 0.8 |
| 130 | 6 | 94 | * | 0.7 | 1.4 | 0.9 | 0.8 | 1.0 |
| 131 | 4 | 96 | * | 0.4 | 1.2 | 1.0 | 0.9 | 1.0 |

*Sample does not freeze immediately. In other words, the sample slowly solidifies at room temperature and will set up in about twenty-four hours or thereabouts at room temperature. None of the other forms of vitamin E seem to polymerize over a period of time.
Comparisons with cosmetic sticks.
+ Compared with Vaseline.

From Table 9, one can conclude that AT can be combined with GMS to form a substitute for Vaseline or Cosmetic sticks. It would appear that the lower the concentration of the GMS the more like Vaseline is the resulting solution. It is amazing how little GMS it takes to solidify AT.

In view of the fact that D alpha tocopherol is the biologically active form of vitamin E, it is apparent that formulas that contain less than 1% GMS and above 99% AT are the formulas that are closest to pure vitamin E.

TABLE 10

| Formulations that contain GMS, ATA, D alpha tocopherol, and Jojoba oil. Readings are ratios that compare sample properties to Vaseline properties. (Unmixed is "u"; mixed is "m".) | | | | | | | | | |
|---|---|---|---|---|---|---|---|---|---|
| FORMULA | FP | GMS | ATA | AT | JO | GG | HH | DD | II | JJ |
| 132 | 84 | 6 | 3 | 88 | 3 | 1.0 | 1.4 | 0.8 | 0.9 | 1.0 |
| 133 | 104 | 30 | 10 | 50 | 10 | 2.0 | 2.0 | 0.5 | 0.4 | 0.5 |

TABLE 10-continued

Formulations that contain GMS, ATA, D alpha tocopherol, and Jojoba oil. Readings are ratios that compare sample properties to Vaseline properties. (Unmixed is "u"; mixed is "m".)

| FORMULA | FP | GMS | ATA | AT | JO | GG | HH | DD | II | JJ |
|---|---|---|---|---|---|---|---|---|---|---|
| 134 | 96 | 10 | 10 | 20 | 60 | oil separates, particulate not homogeneous | | | | |
| 135 | 114 | 50 | 40 | 5 | 5 | 3.0 | 1.0 | 0.5 | 0.2 | 0.2 |
| 136 | 105 | 25 | 60 |  | 15 | u 1.5 | u 1.5 | u 0.4 | m 0.1 | u 0.3 |
|  |  |  |  |  |  | m 1.0 | m 2.0 | m 0.4 |  | m 0.2 |
| 137 | 102 | 25 | 40 | 20 | 15 | u 1.6 | u 1.5 | u 0.5 | m 0.2 | u 0.4 |
|  |  |  |  |  |  | m 1.3 | m 2.0 | m 0.5 |  | m 0.3 |
| 138 | 93 | 15 | 65 |  | 15 | u 1.3 | u 1.4 | u 0.6 | m 0.5 | u 0.7 |
|  |  |  |  |  |  | m 1.2 | m 2.0 |  |  | m 0.9 |
| 139 | 90 | 15 | 30 | 35 | 20 | u 1.3 | u 1.3 | u 0.7 | m 0.5 |  |
|  |  |  |  |  |  | m 1.0 | m 1.3 | m 0.7 |  |  |
| 140 | 104 | 20 | 60 |  | 20 | u 1.5 | u 1.5 |  | m 0.2 | m 0.7 |
|  |  |  |  |  |  | m 1.1 | m 1.7 | m 0.9 |  |  |
| 141 | 93 | 20 | 30 | 30 | 20 | u 1.1 | u 1.2 |  | m 0.3 | m 0.8 |
|  |  |  |  |  |  | m 1.0 | m 1.0 | m 0.9 |  |  |

From Table 10, it is concluded that:
1. It is possible to make compositions having the following ingredients and concentrations of ingredients:
   a. GMS 6 to 50 grams in 100 grams of said compositions,
   b. ATA 3 to 60 grams in 100 grams of said compositions,
   c. AT 5 to 88 grams in 100 grams of said compositions,
   d. Jojoba oil 3 to 60 grams of said compositions.

The above ingredients and concentrations in the above compositions indicate that AT can be substituted for any part of the ATA in all the compositions described in this application.

TABLE 11

| FORMULA | GMS | AT | JO | GG | HH | II | DD | JJ | FP |
|---|---|---|---|---|---|---|---|---|---|
| 142 | 5.8 | 89 | 5.2 | 1.0 | 1.0 | 1.0 | 0.8 | 0.8 | 84 |
| 143 | 4.8 | 73.2 | 22 | 0.5 | 1.0 | 1.0 | 0.8 | 1.0 |  |
| 144 | 11 | 67 | 22 | 1.5 | 1.4 | 0.2 | 0.8 | 0.7 | 92 |
| 145 | 9.2 | 56 | 34 | 1.5 | 1.0 | 0.2 | 0.8 | 0.6 | 94 |
| MIXED |  |  |  |  |  |  |  |  |  |
| 146 | 45.6 | 45.6 | 8.8 | 3.0 | 3.0 | 0.1 | 0.3 | 0.3 | 102 |
| 147 | 39.6 | 39.6 | 20.9 | 2.5 | 3.0 | 0.1 | 0.5 | 0.5 | 98 |

Formulation 142 was unusually clear or transparent. It is just as transparent as Vaseline. In addition, it is just as hard as Vaseline, and it is just about as tack free as Vaseline. Adding more Jojoba oil to 142 produces formula 143. Additional Jojoba oil only decreases the hardness of formula 142. Formula 142 is indeed remarkably like Vaseline except for its deep golden color and slightly reduced ability to lubricate. However, it suffers from one major disadvantage: it has an obnoxious odor. The addition of ATA to AT and Jojoba oil preparations alleviates the odor problem. It is the need to provide an odor free and crystal clear, transparent composition that explains the need for formulations that have both AT and ATA.

The three cosmetic bases described above are actually much more complicated than indicated. This is true because vitamin E is actually a group of compounds which are classifed as follows and because these types of vitamin E are manufactured differently. These types of vitamin E are classified as follows:
1. ATA (manufactured chemically). Since it is manufactured chemically it contains two isomers, dextro and levo.
2. The mixed tocopherols (alpha, beta, gamma and delta)
3. Dextro alpha tocopherol. Manufactured from natural oils (soya) by distillation. Unfortunately, distillation cannot produce an absolutely pure vitamin E. Some soya oil is left.

The following data is derived from compositions that use the purest possible D alpha tocopherol. Up to 33% of D alpha tocopherol may be soya oil. However, the D isomer is the natural configuration and is therefore the only isomer used by living tissue. In addition, D alpha tocopherol is the biologically active form of vitamin E on the market despite the presence of some soya oil in the distillate. Thus, D alpha tocopherol may be the preferred or the most potent form of vitamin E to use for preparing a cosmetic that has the highest concentration of vitamin E. However, it suffers from some serious disadvantages: (a) it has an obnoxious odor; and (b) it is more easily oxidized. ATA is much more resistant to oxidation.

There is a solution to the first problem. Solutions that are composed of 33 grams D alpha tocopherol and 66 grams of D and L ATA and then combined with GMS with the aid of enough heating to melt the GMS and enough mixing to produce a homogeneous solution will upon cooling to room temperature be devoid of an obnoxious odor. Thus, mixtures of ATA and AT may be important to the future of cosmetics.

Some of the types of compositions that can be prepared from GMS, ATA, AT and the mixed tocopherols are described as follows:
1. GMS pure and AT (see Table 7),
2. GMS and mixed tocopherols (see Table 7),
3. GMS and ATA (see Table 7),
4. GMS, AT and ATA,
5. GMS, AT and mixed tocopherols,
6. GMS, AT, ATA, and the mixed tocopherols,
7. GMS, ATA and mixed tocopherols.

However, an examination of the data indicates that the mixed tocopherols produce solutions that are quite like AT solutions. This is substantiated by the fact that the mixed tocopherols are made mostly of AT, and by the fact that the mixed tocopherols and AT are both the product of the distillation process. Thus, the mixed tocopherols and AT are contaminated with about the same quanitity of soya oil. Finally, it must be born in mind that the big reason for the differences between ATA solutions and AT solutions is probably the contamination of the natural vitamin solutions with soya oil or whatever oil is used as a base to extract vitamin E.

When one considers the information in the last paragraph, one realizes that the above list of possible types of vitamin E solutions is reduced to the following: (a) GMS and ATA (Tables 1, 3, 6 and 8): (b) GMS and the natural vitamin E mixtures (Tables 6, 8, and 9); (c) GMS, natural vitamin E and ATA (Table 7); (d) GMS, ATA and Jojoba oil (Tables 2, 3, and 5); (e) GMS, natural vitamin E and Jojoba oil (Table 11); (f) GMS, natural vitamin E, ATA and Jojoba oil (Table 10).

We have thus far described a group of compositions that represent the foundations for a new cosmetic base or a new base for suspending therapeutic reagents. A new cosmetic base is defined as a group of compounds that can be put together in a variety of ways in order to make a variety of different cosmetics. This application describes the many ways of putting a new group of ingredients together and the many considerations that have to be considered in putting these ingredients together in order to produce the full range of cosmetics, from lipsticks to a hand lotion. Many of these considerations have been discussed above.

There are additional basic requirements for a cosmetic base: (1) the cosmetics that are produced from the group of ingredients that define the cosmetic base must not separate in storage and under a variety of climatic conditions; (2) the ingredients must not turn rancid or deteriorate into toxic or odorous compounds; (3) the ingredients must be put together in such a way that will make them stable over a long period of time; (4) the compositions that are produced can be sterilized; (5) bacterial will not grow in the resulting compositions; (6) the ingredients of the group of compounds that represent the cosmetic base must be non-toxic and biodegradeable and a normal part of living biochemical pathways; (7) the cosmetic base must have the highest possible concentration of vitamin E. In fact, it must have such a high concentration of vitamin E that one could use it instead of using pure vitamin E. In other words, the resulting cosmetic must be able to satisfy the presently felt need of many people to put pure vitamin E on the skin. This application describes cosmetic bases that are as close as possible to pure vitamin E. There is a need for such cosmetic bases, because pure vitamin E is a viscous oil and is therefore a poor cosmetic. The present invention teaches how to transpose pure vitamin E directly into cosmetics or cosmetic bases.

The resulting base can also be used to suspend a variety of therapeutic agents that could be considered dermatological medications. The resulting product would therefore be considered a dermatological medication. For example, antibiotics could be suspended in the above described cosmetic bases. This raises another requirement. The resulting bases must be viscous enough to prevent separation of solid or liquid ingredients that are added to said bases. All of the compositions that are disclosed herein are viscous enough to suspend solid or liquid additives. I shall now describe some beneficial products that can be produced by adding a variety of ingredients to the above described cosmetic or therapeutic bases.

A good stick cosmetic has to be soft enough to leave a small amount of cosmetic on the skin when it is rubbed on the skin. However, it should not be so soft that globs or large pieces are left on the skin; hardness is of great importance to a stick cosmetic. In addition, a good stick cosmetic should seem to be slippery. Thus, they are also good lubricants. The lubrication ability makes it easier to rub off the cosmetic on the skin without applying too much pressure; a cosmetic stick that requires a large amount of pressure is not a good cosmetic stick. Thus, the pressure required while applying a stick is an important criterion for evaluating cosmetic sticks. The amount that rubs off is also a vital criterion for evaluating stick cosmetics, especially if too much is put on the skin. The factor that is most likely to cause excess material to come off is a tendency for the stick to crumble or fall apart under the pressure needed to apply the cosmetic.

Table 13, below, describes two types of cosmetic sticks: (1) cosmetic sticks made from GMS and vitamin E and, (2) cosmetic sticks made from GMS, vitamin E and Jojoba oil. The term vitamin E refers to ATA, AT, or the mixed tocopherols, or any possible combination of the different types of vitamin E. The criteria used to describe the experimental sticks are the criteria described above. These criteria are: (1) hardness, (2) tack, (3) lubrication, (4) pressure, and (5) amount removed by a single stroke of the finger.

The above criteria are measured by comparing the experimental sample with the three best cosmetic sticks already on the market. The experimental stick that is equivalent to the average of the cosmetic sticks that are currently being sold will be given a reading of 1. Those samples with properties higher or lower than the average of the above three cosmetic sticks will be given a reading that is higher or lower than 1. Thus, a sample that is given a reading of 1.5 under the vertical column entitled "hardness" will be 1.5 times as hard as the average of the hardness of the above three commercially sold cosmetic sticks. All readings are the average of the personal opinion of three separate observers. Thus, for example, three separate observers compared the tack of each separate experimental sample with the tack of the above three samples and determined the relative tack of the experimental sample. The same procedure was followed for hardness, lubrication, amount removed, and pressure required for applying sample to the skin.

While such a method of measurement may seem non-objective, it should be kept in mind that the suitability of a cosmetic is a purely subjective matter. Only a user of a cosmetic can determine just how hard she must press in order to apply the stick cosmetic, and the amount deposited will depend on how hard the person applies the stick. In addition, the ease with which the person applies the cosmetic will depend on how hard one presses the stick. Thus, the whole subject is subjective and measurements are best made by compiling an average of subjective opinions. Such averages are more likely to be closer to the opinions of the average public user.

The following concerns the fact that GMS and vitamin E solutions are high viscosity solutions. This is indicated by the fact that most of the solutions described herein have viscosities that are as high as or are higher than, the viscosity of Vaseline. It is known that the viscosity of Vaseline is such that finely ground particles (minus 200 mesh) can be suspended in the Vaseline without fear that the particles will separate out. I will now consider the benefits of suspending or dissolving a variety of solids or liquids into the cosmetic bases of this invention, and I shall first discuss the difference between dissolving and suspending ingredients in the above bases.

A variety of dyes have been approved for use in drugs and cosmetics, such as D and C red #6 BA LAKE, D and C red #7 AL LAKE, and D and C red #7 CA LAKE. A series of tests were run to see if these dyes, and all such dyes, are soluable in the above bases. It was concluded that: (1) some of the D and C dyes are soluable in all of the possible solutions that can be prepared from the above described bases; (2) further tests showed that the D and C colors are only slightly soluable in vitamin E or Jojoba oil or vitamin E and Jojoba oil. However, the D and C dyes are very soluable in GMS. Since GMS is a common element in all of the above bases we can understand why the D and C dyes are soluable in all of the above bases. It seems that the dyes may be added to the molten GMS and mixed until a homogeneous solution is attained. The molten GMS and dye can then be easily dispersed into the vitamin E or vitamin E and Jojoba oil for compositions with only a low concentration of GMS. The dye can also be added to molten solutions that have GMS and vitamin E or GMS, vitamin E and Jojoba oil, and mixed into the molten solutions.

The fact that the D and C dyes are soluable in the above bases makes it possible to prepare lipsticks and rouges from the above bases. In addition, it is possible to prepare a product called "extra shine lip gloss". Lip gloss does not come in a stick. It is provided in a tray, and the user dips it out of the tray with her finger and applies it with the finger. The following formulation duplicates lip gloss. A formulation (formula 148) comprises 10 grams GMS, 90 grams ATA and up to five grams of D and C red #6 duplicates lip gloss and has a freezing point of 94° F. The most amazing thing about formula 142 is its mirror-like surface after the molten solution freezes. Even after the frozen solution is mixed, its surface is almost unbelievably reflective. Furthermore, high reflectivity is limited to solutions that have less than 20 grams GMS in 100 grams of GMS, ATA and dye solution. The higher the concentration of GMS formula, the lower the reflectivity. This raises the question of how one increases the reflectivity of lipsticks; lipsticks contain the same ingredients as lip balm except that the GMS concentrations are higher (see below). This question will be considered after the discussion of lipsticks below. Table 12 describes properties of formula 148 in greater detail. The numbers in Table 12 are ratios between formula 148 and several commercial lip balm products. Thus, the number 1 means that formula 148 is the same as the commercial lip balms relative to the characteristics listed in the vertical column. Also a number larger than 1 means that the formula 148 characteristic is higher than that of the average lip balms on the market and vise versa.

TABLE 12

| FORMULA | HARDNESS | TACK | REFLECTION | SPREAD-ABILITY | LUBRI-CATION | PRES-SURE | AMOUNT RUBBED OFF |
|---|---|---|---|---|---|---|---|
| 148 | 0.8 | 1 | 1 | 1 | 1 | 1 | 1 |

As can be seen from Table 12, formula 148 is an almost perfect match for the average of several lip gloss formulations currently being sold on the market.

Lipsticks have one major problem. They must be hard enough to support the pressure applied when they are rubbed on the skin. In addition, light pressure should be required to remove just the right amount of lipstick from the stick or apply just the right amount of lipstick to the lips. If too much pressure is required to apply too little lipstick, the stick will have to be made softer. A hard stick that has a very slippery surface and which applies just the right amount of lipstick is the ideal stick.

In Tables 13 and 14, the headings KK, LL, NN, OO, PP, QQ and RR designate, respectively, tack, coverage, hardness, reflectivity, rub-off, slip and pressure characteristics as ratios with the average of the characteristics of commercial products as described above. Heading MM designates freezing point in degrees Fahrenheit. The quantities listed under GMS, ATA, D and C red #6 and Jojoba oil are the amount in grams. In Table 14 the amount under "Iron Oxide" is in grams.

TABLE 13

| LIPSTICKS | | | | | | | | | | | |
|---|---|---|---|---|---|---|---|---|---|---|---|
| | | | | Comparison with commercial lipsticks | | | | | | | |
| FORMULA | GMS | ATA | D & C* | KK | LL | MM | NN | OO | PP | QQ | RR |
| 149 | 20 | 80 | 1 | 1 | | 99 | 0.7 | 0.7 | 0.5 | 0.7 | 1.5 |
| 150 | 25 | 75 | 2 | 1.3 | 0.5 | 103 | 0.8 | 0.8 | 0.5 | 0.8 | 1.4 |
| 151 | 30 | 70 | 2 | 1.5 | 0.6 | 104 | 1.0 | 0.9 | 0.4 | 0.7 | 1.5 |
| 152 | 40 | 60 | 4 | 1.6 | 0.8 | 110 | 1.4 | 0.5 | 0.3 | 0.3 | 2.0 |
| The following samples are the same as formulas 150, and 152 except they are mixed until there are no lumps. | | | | | | | | | | | |
| 153 | 25 | 75 | 2 | 2.0 | 0.8 | 99 | 0.3 | 1.0 | 2.0 | 0.6 | 0.5 |
| 154 | 30 | 70 | 2 | 3.0 | 0.7 | 103 | 0.7 | 0.8 | 3.0 | 0.5 | 0.5 |
| 155 | 40 | 60 | 4 | 1.8 | 0.4 | 110 | 0.9 | 0.3 | 0.3 | 0.3 | 2.0 |
| The following sample shows the effect of Jojoba oil and ATA (unmixed sample). | | | | | | | | | | | |
| FOR. | GMS | JO | ATA | D & C* | | | | | | | |
| 156 | 30 | 35 | 35 | 2 | 1.0 | 0.6 | 110 | 1.0 | 1.0 | 0.8 | 1.0 | 1.0 |

*D and C Red #6 Barium Lake 62%

Mixing the last sample produces a composition that has the same physical qualities except that the amount rubbed off exactly equals that of the average lipstick. And the coverage also equals the coverage of the average lipstick. Thus, I have succeeded in duplicating the average lipstick with GMS, vitamin E, Jojoba oil and the dyes that are usually added to lipsticks.

Some commercial lipsticks are more opaque and have better ability to hide the surface of the skin. One can improve the opacity of the above lipsticks by adding talc, magnesium carbonate, the iron oxides and other fillers. These fillers do not become absorbed into the above bases, but merely become suspended therein. The talc and magnesium carbonate have little effect on the physical attributes of the bases. However, the iron oxide pigments have a significant effect on the physical qualities of the bases.

The following Table shows the effects of iron oxide pigments—red, yellow, black and blue.

TABLE 14

| FORM | GMS | JO | ATA | D & C | IRON OXIDE | KK | LL | MM | NN | OO | PP | QQ | RR |
|---|---|---|---|---|---|---|---|---|---|---|---|---|---|
| 157 | 30 | 35 | 35 | 2 | 1 | 1.0 | 0.7 | 111 | 1.0 | 1.0 | 0.8 | 0.8 | 1.4 |
| 158 | 30 | 35 | 35 | 2 | 1 | 1.5 | 1.0 | 110 | 0.8 | 1.0 | 1.4 | 1.0 | 1.0 |
| 159 | 30 | 35 | 35 | 2 | 3 | 1.2 | 0.7 | 110 | 1.2 | 0.6 | 0.4 | 0.8 | 1.8 |
| 160 | 30 | 35 | 35 | 2 | 3 | 1.6 | 1.0 | 110 | 0.6 | 0.6 | 1.8 | 0.8 | 1.0 |

Formula 157 is unmixed, while formula 158 is mixed.

The biggest effect of adding 3% iron oxide pigments is the color which varies from deep brown to a darker red. More important is the decrease in rub-off and the increase in required pressure.

All things considered, an iron pigment concentration of approximately 1% may have an optimum of benefits in terms of increasing the opacity and a minimum of detrimental effects. However, colorless pigments can go much higher. For example, up to 50 grams of talc can easily be suspended in 100 grams of the above bases. The effects are always the same no matter what the pigment. The result is a harder, more viscous and less reflective coating. However, these effects can be countered in part by simply adding less GMS.

There is one way to recognize a suspension: the freezing point does not change. If one is dealing with a suspension, there will be very little effect on freezing point from suspending approximately 1% solids in the above bases. This last point is extremely important because it means that the above described compositions also describe the same solutions after 1% to 2% of a finely ground solid is suspended in the matrix of the base.

The most sensitive system of all is the lipstick system. Even here, a 1% addition of pigments still produces a usable product that is almost exactly the same as the product without the pigment. Thus, when we are dealing with a substitute for Vaseline, the addition of a solid at the 1% concentration will have almost no detectable effect on the viscosity or spreadability and the like.

There is a difference between the freezing point of solutions that have dyes and equivalent solutions that do not have dyes. This is true because the dyes are soluable in the above bases.

All of the above work on lipsticks was done with D and C color #6. Some preliminary work was also done with D and C dye #27 and D and C dye #7. The results indicate that these other dyes are also usable in lipstick based on the cosmetic bases described herein. The big difference between these dyes seems to be the color they impart on the herein described bases. D and C #7 and D and C #27 compositions are purple, whereas D and C dye #6 produces a reddish color when combined with the above described bases.

Vitamin E is alleged to be an aid to healing. Solidified vitamin E, as described above, may also prove to be an aid to healing wounds. The following therapeutic additivies have been combined with the following formulations:

| Formula Numbers | Ingredient Added | Amount Added |
|---|---|---|
| 7, 11, 15, 44, 46, 50, 142 | Neomycinsulfate | 1 gram in 100 grams formula |
| 7, 11, 15, 44, 46, 50, 142 | Polymyxin B Sulfate | 1 gram in 100 grams formula |
| 7, 11, 15, 44, 46, 50, 142 | Allantoin | 1 gram in 100 grams formula |
| 7, 11, 15, 44, 46, 50, 142 | Methyl and propy Pareben | 1 gram in 100 grams formula |
| 7, 11, 15, 44, 46, 50, 142 | Hydroxy cortisone | 1 gram in 100 grams formula |
| 7, 11, 15, 44, 46, 50, 142 | Estrone | 1 gram in 100 grams formula |
| 7, 11, 15, 44, 46, 50, 142 | Vitamin A | 1 gram in 100 grams formula |

The first five listed additives resulted in no change in properties. The addition of vitamin A, however, resulted in a number of changes. The freezing point fell about three to five degrees Fahrenheit. Viscosities went down, but this could be compensated by adding more GMS. Solutions become more transparent. Thus, adding vitamin A is another path towards solutions that are more transparent.

Table 15 shows additional examples of stick cosmetics. The headings "HARDNESS", "TACK", "LUBRICATION", "PRESSURE", and "AMOUNT RUBBED OFF" represent these factors as defined above.

TABLE 15

STICK COSMETICS

| FORM | GMS* | ATA* | JO* | HARDNESS | TACK | LUBRICATION | PRESSURE | AMOUNT RUBBED OFF |
|---|---|---|---|---|---|---|---|---|
| 161 | 25 | 75 | | 0.7 | 1.8 | 0.7 | 1.3 | 0.8 |
| 162 | 30 | 70 | | 1.0 | 1.3 | 0.8 | 1.5 | 0.3 |
| 163 | 40 | 60 | | 1.2 | 1.5 | 0.8 | 2.0 | 0.3 |
| 164 | 50 | 50 | | 2.0 | 1.0 | 0.5 | 3.0 | 0.1 |
| 165 | 60 | 40 | | Too hard for a stick | | | | |
| 166 | 20 | 35 | 45 | Too soft for stick | | | | |
| 167 | 28 | 28 | 44 | 1.0 | 1.0 | 1.0 | 1.0 | 1.5 |
| 168 | 30 | 20 | 50 | 1.0 | 1.0 | 1.0 | 1.0 | 1.3 |
| 169 | 40 | 10 | 50 | 1.0 | 1.0 | 1.0 | 1.0 | 1.0 |
| 170 | 40 | 50 | 10 | 1.0 | 1.0 | 1.0 | 1.0 | 1.3 |
| 171 | 50 | 25 | 25 | 1.3 | 1.0 | | | |
| 172 | 60 | 10 | 30 | 3.0 | 1.0 | 0.4 | 3.0 | 0.2 |
| 173 | 60 | 30 | 10 | 3.0 | 1.0 | 0.5 | 1.5 | 0.4 |
| 174 | 70 | 10 | 20 | 4.0 | 1.0 | 0.3 | 3.5 | 0.2 |
| 175 | 70 | 20 | 10 | 3.5 | 1.0 | 0.5 | 3.0 | 0.3 |

TABLE 15-continued
STICK COSMETICS

| FORM | GMS* | ATA* | JO* | HARDNESS | TACK | LUBRICATION | PRESSURE | AMOUNT RUBBED OFF |
|---|---|---|---|---|---|---|---|---|
| 176 | 50 | 10 | 40 | 1.5 | 1.0 | 0.5 | 2.0 | 0.4 |
| 177 | 50 | 40 | 10 | 1.5 | 1.0 | 0.7 | 1.5 | 0.5 |

*In grams

I have also investigated the use of glyceryl distearate (GDS) as a substitute for GMS in the formulations of the present invention. In Table 16, below, characteristics for unmixed and mixed solutions are indicated in the table for a particular formulation.

TABLE 16

| FORM. | GDS* | JO* | ATA* | HARDNESS | TACK | TRANSPARENCY | LUBRICITY |
|---|---|---|---|---|---|---|---|
| 178 | 10 | 40 | 50 | Oil separates | | | |
| 179 | 10 | 30 | 60 | 1.0 | 1.2 | 0.8 | 0.8 |
| 180 | 10 | 20 | 70 | 0.7 | 1.7 | 0.9 | 0.7 |
| 181 | 10 | 10 | 80 | 1.0 | 2.0 | 1.0 | 0.6 |
| 182 | 5 | 5 | 90 | Liquid | | | |
| 183 | 15 | 20 | 65 | 2.0 u | 1.5 | 0.3 | 0.5 |
| | | | | 1.0 m | 2.5 | | |
| 184 | 20 | 30 | 50 | 3.0 u | 1.0 | 0.3 | 1.0 |
| | | | | 2.0 m | | | |
| 185 | 20 | 10 | 70 | 2.0 u | 2.5 | 0.3 | 0.7 |
| | | | | 1.5 m | | | |
| 186 | 30 | 20 | 50 | 3.0 u | 1.5 | 0.1 | 0.9 |
| | | | | 1.5 m | 2.0 | | |
| 187 | 30 | 10 | 60 | 3.0 u | 2.0 | 0.1 | 0.2 |
| | | | | 2.0 m | 3.0 | 0.1 | 0.1 |
| 188 | 30 | 50 | 20 | 2.5 u | 1.0 | 0.1 | |
| | | | | 1.5 m | 1.5 | 0.1 | |
| 189 | 20 | 60 | 20 | 3.0 u | 1.0 | 0.1 | 1.0 |
| | | | | 2.0 m | | | |

*In grams

Formulations 178–181 have the greatest similarity to Vaseline. This is true, because these are the samples that are most transparent. Samples 180 and 181, however, have fairly high tack. This leaves sample 179 as the best substitute for Vaseline.

Formulations 186, 187 and 188 (unmixed) are good sticks. Formulation 188 (mixed) is good as a Vaseline substitute. Formulation 189 (mixed) crumbles under finger pressure.

A comparison between Table 1 and Table 16 indicates that GDS compositions are harder than GMS compositions. For example, compare sample 15 with sample 184 above. GDS samples also seem to have higher tack; compare the same two samples.

From a comparison of sample 16 with sample 185, it becomes obvious that GDS compositions seem to have lower transparency. This is probably due to the crystalization that can be found in almost all the above samples. Sample 185 was prepared in the hope that low concentrations of Jojoba oil would get away from the crystalization. However, even after mixing, crystalization becomes a problem in a day. GMS samples can be permanently relieved of crystals by: (1) mixing with pressure; and (2) storage for a few days in a moderately warm room. GDS samples cannot be relieved of crystals by the above processes. The only thing that helped was to lower the concentration of GDS to 10% and then mix.

The mixed 10% GDS solutions seem to be permanently relieved of crystals. However, sample 178 shows oil separation. Also samples 180 and 181 are fairly tacky, because they need more Jojoba oil to counteract the tack. The above indicates that GDS solutions have a severly limited range of useful concentrations, if they are used as a substitute for Vaseline.

However, samples 186, 187, and 188 indicate that GDS solutions will be most useful in stick cosmetics. This is supported by the fact that a stick cosmetic must hang together while it is rubbed on the skin. The enormous tendency for GDS to form crystals is the very tendency that will make GDS the ideal hardening agent for stick cosmetics. This is illustrated by the stick cosmetic examples in Table 17.

TABLE 17
STICK COSMETICS WITH GLYCERYL DISTEARATE COMPARED WITH STICK COSMETICS ON THE MARKET

| FORMULA | GDS | JO | ATA | TACK | HARDNESS | REFLECTIVITY | RUB-OFF | SLIP | PRESSURE |
|---|---|---|---|---|---|---|---|---|---|
| 190 | 30 | 10 | 60 | 3.0 | 0.4 | 0.5 | 1.0 | 0.5 | 1.0 |
| 191 | 30 | 50 | 20 | 1.0 | 0.8 | 1.0 | 1.0 | 1.0 | 1.3 |
| 192 | 40 | 10 | 50 | 2.0 | 1.0 | 0.8 | 0.5 | 1.0 | 1.5 |
| 193 | 40 | 40 | 20 | 1.0 | 1.0 | 1.0 | 0.5 | 1.0 | 1.5 |
| 194 | 50 | 10 | 40 | 3.0 | 1.5 | 1.0 | 0.2 | 0.6 | 2.0 |
| 195 | 50 | 30 | 20 | 1.0 | 2.0 | 1.0 | 0.1 | 0.6 | 2.5 |

Thus, GDS solutions do indeed produce tougher sticks than GMS solutions. The lower concentration GDS solutions are most useful. However, with additives such as perfumes, the higher concentration GDS solutions will probably also be most useful.

Table 18 shows the characteristics of GDS and ATA solutions.

TABLE 18

GDS and ATA Solutions Comparison with Vaseline

| FORMULA | GDS Grams | ATA Grams | TACK | HARDNESS | LUBRI-CATION | TRANS-PARENCY | REFLEC-TIVITY |
|---|---|---|---|---|---|---|---|
| 196 | 3 | 97 | | | | | |
| 197 | 5 | 95 | | | | | |
| 198 | 10 | 90 | 1.5 | 1.0 | 1.0 | 1.0 | 1.0 |
| 199 | 20 | 80 | 1.5 | 2.0 | 0.8 | 0.6 | 0.8 |
| 200 | 30 | 70 | 2.0 | 2.5 | 0.5 | 0.2 | 0.3 |
| 201 | 40 | 60 | 3.0 | 3.0 | 0.3 | 0.1 | 0.2 |
| 202 | 50 | 50 | | | | | |
| 203 | 60 | 40 | | | | | |
| 204 | 70 | 30 | | | | | |

Formula 196 remained liquid at room temperatures. Formula 197 flowed at 90° F. Formulas 198, 199 and 200 were good substitutes for Vaseline as indicated. Formulas 201, and 202 were excellent dermatological putties. Formula 202 was too hard to scoop, but could be rolled into a ball. Formula 203 was too hard to scoop and hard to roll into a ball and spread. Formula 204 was too hard to scoop, almost impossible to roll into a ball and, therefore, almost impossible to spread. As can be seen from the above, GMS and GDS produce fairly equivalent solutions with ATA except for slight differences at the lower and higher concentrations of GMS and GDS. It is to be noted that GDS takes time to harden at the lower concentrations.

The above indicates that GDS can be substituted for GMS in most of the formulations that have GMS and ATA. The following explores the possibility of substituting GDS for GMS in some of the other formulations described above.

soft enough to scoop out. From this, it is apparent that the hardening with aging effect depends on whether the samples are mixed.

It is to be noted that the methods used for measuring hardness, tack, reflectance and transparency in this application involved averaging three separate personal opinions. For hardness the following criteria guided such evaluations: (a) the value 1.0 means it is as hard as Vaseline; (b) the value 2.0 means that it is harder than Vaseline, but has the same spreadability as Vaseline and still has the look and feel of Vaseline; (c) the value 3.0 means it is obviously much harder than Vaseline and can be scooped out with one's finger; (d) the value 4.0 means it cannot be scooped out with one's finger, but a spoon or other instrument can be used to scoop out the sample; (e) the value 5.0 means it is almost impossible to scoop out.

Both samples 208 and 209 can be rolled after they are kneaded until there are no hard pieces left and then

TABLE 19

GDS and Alpha Tocopherol Comparison With Vaseline

| FORMULA | GDS Grams | AT Grams | TACK | HARDNESS | LUBRI-CATION | TRANS-PARENCY | REFLEC-TIVITY |
|---|---|---|---|---|---|---|---|
| 205 | 5 | 95 | | | | | |
| 206 | 10 | 90 | | | | | |
| 207 | 20 | 80 | 1.5 | 0.7 | 0.7 | 0.3 | 0.9 |
| 208 | 30 | 70 | 0.0 u | 3.0 u | 0.1 | 0.1 | 0.2 |
|  |  |  | 3.5 m | 4.0 m | | | |
| 209 | 50 | 50 | 0.0 u | 3.5 u | 0.1 | 0.1 | 0.1 |
|  |  |  | 4.0 m | 4.5 m | | | |
| 210 | 60 | 40 | | | | | |

Formulas 205 and 206 were still liquid after overnight storage. Formula 207 was liquid during the first few hours, but solidified overnight. Formula 208 was about as hard as Vaseline during the first few hours, but hardened overnight. Under the "tack" and "hardness" columns for formulas 208 and 209, the figure with a "u" is for the unmixed solution, while the figure with the "m" is for the mixed solution. One-half of these samples were mixed the night before, and the other half were not mixed. The next day the parts that were mixed were so hard that one could not scoop them out with one's finger. However, the part that had not been mixed was spread on the skin. Thus, they are good dermatological putties. The tack figures for samples 208 and 209 indicate no tack for the unkneaded solutions with a large increase in tack resulting from kneading. Formula 210 was too hard to scoop out with a finger. However, it can be rolled into a ball and spread on the skin and is, therefore, a good dermatological putty.

It is clear therefore, that some of the GDS and AT formulations are useful even though the low GDS concentration solutions are liquids.

Table 20 illustrates the characteristics of GDS and mixed tocopherols solutions.

TABLE 20

(GDS) Glyceryl Distearate and the Mixed Tocopherols (MT) Comparison with Vaseline

| FORMULA | GDS Grams | MT Grams | TACK | HARDNESS | LUBRI-CATION | TRANS-PARENCY | REFLEC-TIVITY |
|---|---|---|---|---|---|---|---|
| 211 | 5 | 95 | | | | | |
| 212 | 10 | 90 | | | | | |
| 213 | 20 | 80 | 2.5 | 1.0 | 0.7 | 0.2 | 0.2 |
| 214 | 30 | 70 | 3.0 | 2.0 | 0.6 | 0.1 | 0.1 |

TABLE 20-continued (GDS) Glyceryl Distearate and the Mixed Tocopherols (MT)
Comparison with Vaseline

| FORMULA | GDS Grams | MT Grams | TACK | HARDNESS | LUBRI-CATION | TRANS-PARENCY | REFLEC-TIVITY |
|---|---|---|---|---|---|---|---|
| 215 | 40 | 60 | 0.0 u<br>3.0 m | 3.0 u<br>4.0 m | 0.1 | 0.1 | 0.1 |
| 216 | 50 | 50 | 0.0 u<br>3.0 m | 3.0 u<br>4.0 m | 0.1 | 0.1 | 0.1 |
| 217 | 60 | 40 | 0.0 u<br>2.5 m | 3.5 u<br>4.5 m | 0.1 | 0.05 | 0.05 |

Formulas 211 and 212 are liquid at room temperature. The figures under tack and hardness for formulas 215, 216 and 217 give the results for the unmixed (u) and mixed (m) solutions. Formulas 215 and 216 were good dermatological putties.

The mixed tocopherols and AT solutions are similar. ATA and AT and the mixed tocopherols all produce highly tacky solutions when hardened with GDS. However, it is difficult to counteract this tact with Jojoba oil. This is true because solutions with GDS and Jojoba oil have an almost unbelievable tendency to form crystals. The most undesirable fact about solutions with GDS and Jojoba oil is that one cannot remove the crystals by mixing as can be done with the solutions with GMS and Jojoba oil. This is true, because shortly after one mixes the solutions with GDS and Jojoba oil the crystals reform.

Some persons may be sensitive to large concentrations of vitamin E when it is applied to the skin. It has been found, however, that useful substitutes for Vaseline can be formed with low concentrations of vitamin E. Some examples are shown in Table 21.

TABLE 21

| FORM-ULA | GMS | JO | ATA | FREEZING POINT | TACK | HARDNESS | TRANS-PARENCY | LUBRICATION |
|---|---|---|---|---|---|---|---|---|
| | (Grams) | | | | | | | |
| 218 | 15 | 84 | 1 | 115 | 1.0 | 0.6 | 0.6 | 0.9 |
| 219 | 30 | 69 | 1 | 118 | 1.2 | 1.5 | 0.4 | 0.8 |
| 220 | 40 | 59 | 1 | 120 | 1.2 | 2.0 | 0.3 | 0.7 |
| 221 | 50 | 49 | 1 | 123 | 1.5 | 3.0 | 0.2 | 0.3 |

An examination of the above tables indicates that formulations 10, 15, 17 and 34 are very similar to Vaseline and are excellent lubricants. Since the quantity of ATA in these formulations ranges from 40 to 70 grams in 100 grams of solution, it is clear that for excellent lubricity the quantity of ATA may vary widely and does not need to be above 50% in compositions with these three ingredients. However, in the case of lubricity, the ATA needs to be at least 50% of GMS and ATA solutions with no Jojoba oil.

It is to be noted that in all the above disclosed solutions which include Jojoba oil as an ingredient, the glyceryl stearate helps the Jojoba oil stay in solution.

Thus far, I have been concerned with solutions using DL α-tocopherol acetate, the D form of the mixed tocopherols and the D form of the α-tocopherol. The D isomers are manufactured by living organisms (plants) and are isolated from plant oils by distillation which always leaves a significant percentage of soya oil in the finished product. To this point, whenever I referred to the mixed tocopherols (MT) or α-tocopherol (AT), I referred to the forms thereof with soya oil. There is, however, available a DL α-tocopherol that does not have soya oil, because it is manufactured chemically. However, such a product would have much less D isomer than the D α-tocopherol already described. Nevertheless, the characteristics of DL α-tocopherol solutions are described in Table 22:

TABLE 22

| FORMULA | GMS* | DL α-TOCOPHEROL* | TACK | HARDNESS | TRANSPARENCY | LUBRICATION |
|---|---|---|---|---|---|---|
| 222 | 5 | 95 | 1.1 | 0.6 | 0.9 | 0.7 |
| 223 | 10 | 90 | 1.3 | 0.8 | 0.9 | 0.6 |
| 224 | 15 | 85 | 1.8 | 1.0 | 0.8 | 0.4 |
| 225 | 30 | 70 | 2.1 | 2.0 | 0.5 | 0.3 |
| 226 | 50 | 50 | 3.0 | 3.0 | 0.1 | 0.1 |

*In grams

As can be seen from Table 22, DL α-tocopherol compositions are very similar to DL α-tocopherol acetate compositions and, moreover, have no unpleasant odor (probably because of the absence of soya oil).

There are also available a D α-tocopherol acetate with physical characteristics exactly like those of the α-tocopherol acetate which has already been described. The D α-tocopherol acetate can also be used in the solutions of the invention.

All of the solid or semi-solid formulations in Tables 1–22, inclusive, can be scooped out with one's finger with ease and can also be smoothly spread on the skin in thick or thin layers with ease without crumbling much as Vaseline is spread on the skin unless it is otherwise stated.

Where both freezing points and melting points are given, the melting points were determined by measuring the temperature as a solid solution became liquid. In all other cases, all melting points were determined by measuring the temperature at which the molten solution became solid.

While preferred embodiments of the invention have been shown and described, it will be apparent to those skilled in the art that changes can be made without departing from the principles and spirit of the invention, the scope of which is defined in the appended claims.

I claim:

1. A dermatological coating material prepared by combining at least 3 parts by weight of a glyceryl stearate with up to 97 parts by weight of vitamin E component to form a solution with the aid of heat, which solution, when cooled, forms a frozen solution at room temperature, wherein said glyceryl stearate is selected from the group consisting of glyceryl monostearate and glyceryl distearate.

2. A dermatological coating material as recited in claim 1, wherein said glyceryl stearate is at least 10 parts by weight of glyceryl distearate.

3. A dermatological coating material as recited in claim 1, wherein said glyceryl stearate is glyceryl monostearate.

4. A dermatological coating material as recited in claim 3, wherein said glyceryl monostearate and said vitamin E component are mutually soluable.

5. A dermatological coating material as recited in claim 3, wherein said frozen solution further comprises at least 3 parts by weight of Jojoba oil.

6. A dermatological coating material as recited in claim 5, the preparation of the material including subjecting said frozen solution to a mixing under pressure step to reduce crystal formation.

7. A dermatological coating material as recited in claim 5, comprising at least 10% glyceryl monostearate pure and wherein said Vitamin E component comprises at least 60% α-tocopherol acetate.

8. A dermatological coating material as recited in claim 5, comprising at least 20% glyceryl monostearate.

9. A dermatological coating material as recited in claim 5, which resembles solid petrolatum, and comprises 20 parts by weight of glyceryl monostearate, 40 parts by weight of Jojoba oil, and 40 parts by weight α-tocopherol acetate.

10. A dermatological coating material as recited in claim 5, which resembles solid petrolatum, and comprises 15 to 50 parts by weight of glyceryl monostearate, 84 to 49 parts by weight of Jojoba oil, and one part by weight of α-tocopherol acetate.

11. A dermatological coating material as recited in claim 3, wherein said dermatological coating material is a cosmetic foundation and said vitamin E component is α-tocopherol acetate.

12. A dermatological coating material as recited in claim 11, which resembles solid petrolatum and comprises five to 30 parts by weight of glyceryl monostearate and 95 to 70 parts by weight of α-tocopherol acetate.

13. A dermatological coating material as recited in claim 3, said dermatological coating material being a dermatological putty and comprising 30 to 80 parts by weight of glyceryl monostearate and 70 to 20 parts by weight of α-tocopherol acetate.

14. A dermatological coating material as recited in claim 13, said dermatological coating material being a dermatological putty and wherein said glyceryl monostearate comprises at least 40% by weight of said solution and wherein said vitamin E component comprises α-tocopherol acetate, said solution being subjected to a mixing under pressure step by kneading said solution to reduce crystal formation to improve the spreadability and tack of the solution.

15. A dermatological coating material as recited in claim 14, further comprising up to 9.09 percent clove oil as a germicidal agent.

16. A dermatological coating material as recited in claim 3, further comprising up to 9.09 percent clove oil as a germicidal agent.

17. A dermatological coating material as recited in claim 3, wherein the vitamin E component comprises α-tocopherol acetate predominantly and approximately two parts by weight of a component from the group consisting of α-tocopherol and mixed tocopherols to improve the anti-oxidant properties of the solution, said solution being odor free.

18. A dermatological coating material as recited in claim 3, said material being a hair groomer comprising from three to 35 parts by weight of said glyceryl monostearate and from 97 to 65 parts by weight of said vitamin E component.

19. A dermatological coating material as recited in claim 18, wherein said solution is subjected to the step of kneading to soften said solution.

20. A dermatological coating material as recited in claim 3, said material being a hair groomer and wherein said material further comprises at least 10 parts by weight of Jojoba oil.

21. A dermatological coating material as recited in claim 20, wherein said glyceryl monostearate comprises 10 to 20 parts by weight, said vitamin E component is α-tocopherol acetate and comprises 80 to 55 parts by weight and the Jojoba oil comprises 10 to 25 parts by weight.

22. A dermatological coating material as recited in claim 3, said material being a lubricant resembling solid petrolatum and further comprising Jojoba oil, said glyceryl monostearate comprises 20 to 25 parts by weight, said Jojoba oil comprising 60 to 35 parts by weight and said vitamin E component being α-tocopherol acetate and comprising 20 to 40 parts by weight.

23. A dermatological coating material as recited in claim 3, further comprising at least 3 parts by weight of Jojoba oil and wherein said Vitamin E component comprises at least 3 parts by weight of α-tocopherol acetate and at least 5 parts by weight of α-tocopherol, said α-tocopherol increasing the transparency of said material and said α-tocopherol acetate masking the odor of said α-tocopherol.

24. A dermatological coating material as recited in claim 3, further comprising Jojoba oil and wherein said Vitamin E component comprises α-tocopherol acetate and α-tocopherol, said α-tocoperol increasing the transparency of said material and said α-tocopherol acetate masking the odor of said α-tocopherol, wherein said glyceryl monostearate comprises six to 50 parts by weight, said α-tocopherol acetate comprises three to 60 parts by weight, said α-tocopherol comprises five to 88 parts by weight and said Jojoba oil comprises three to 60 parts by weight.

25. A dermatological coating material as recited in claim 3, said material being a cosmetic base.

26. A dermatological coating material as recited in claim 3, said material being a stick cosmetic.

27. A dermatological coating material as recited in claim 26, said material being a lipstick.

28. A dermatological coating material as recited in claim 3, said material being a lip gloss.

29. A dermatological coating material as recited in claim 3, wherein said material is a sexual lubricant.

30. A dermatological coating material as recited in claim 1, wherein said glyceryl stearate is 30 to to 80 parts by weight of a glyceryl distearate and said coating material is a stick cosmetic.

31. A dermatological coating material as recited in claim 1, wherein said solution further comprises a therapeutic agent, said therapeutic agent being selected from the group consisting of neomycinsulfate, polymyxin B sulfate, allantoin, methyl and propyl pareben, hydroxy cortisone, estrone, and vitamin A.

32. A dermatological coating material as recited in claim 1, wherein said glyceryl stearate comprises glyceryl monostearate, said vitamin E component comprises α-tocopherol acetate, and said preparation of said material including the step of mixing said frozen solution under pressure.

33. A dermatological coating material as recited in claim 32, wherein said mixing of said frozen solution is effected in a ball mill.

34. A dermatological coating material as recited in claim 1, wherein said glyceryl stearate comprises at least 6 parts by weight of glyceryl monostearate, said vitamin E component comprises at least 3 parts by weight of α-tocopherol acetate and at least 5 parts by weight of α-tocopherol, and said solution further comprises at least 3 parts by weight of Jojoba oil, said α-tocopherol counteracting the tendency of said Jojoba oil to make said solution opaque.

35. A stable frozen solid or semi-solid vitamin E solution which is made by dissolving at least 3 parts by weight of a glyceryl stearate selected from the group consisting of glyceryl monostearate and glyceryl distearate and up to 97 parts by weight of vitamin E component into one another with the aid of heat and mixing to achieve a homogeneous molten solution which upon cooling to room temperature will form said stable frozen solid or semi-solid vitamin E solution which will not separate into its components on storage.

36. A method of making a vitamin E composition comprising combining at least 3 parts by weight of of glyceryl monostearate with up to 97 parts by weight of a vitamin E component to form solution with the aid of heat, permitting said solution to cool to form a frozen solution under pressure, and mixing said frozen solution to reduce crystal formation.

37. A method of hardening vitamin E into a stable frozen solid or semi-solid solution, comprising the steps of:
 a. dissolving at least 3 parts by weight of a glyceryl stearate selected from the group consisting of glyceryl monostearate and glyceryl distearate and up to 97 parts by weight of vitamin E component into one another with the aid of heat and mixing to achieve a homogeneous molten solution; and
 b. cooling said molten solution to room temperature so that said solution forms said stable frozen solid or semi-solid vitamin E solution which will not separate into its components on storage.

38. A method as recited in claim 37, wherein said glyceryl stearate is glyceryl monostearate.

39. A method as recited in claim 38, wherein said vitamin E component is α-tocopherol acetate.

40. A method as recited in claim 38, wherein said vitamin E component is α-tocopherol.

41. A method as recited in claim 38, wherein said vitamin E component is mixed tocopherols.

42. A method as recited in claim 37, wherein said glyceryl stearate is glyceryl distearate.

* * * * *